United States Patent
Petersen

(10) Patent No.: US 12,144,975 B2
(45) Date of Patent: Nov. 19, 2024

(54) HEART PUMP DRIVELINE POWER MODULATION

(71) Applicant: TC1 LLC, St. Paul, MN (US)

(72) Inventor: Ethan F. Petersen, Oakland, CA (US)

(73) Assignee: TC1 LLC, St. Paul, MN (US)

( * ) Notice: Subject to any disclaimer, the term of this patent is extended or adjusted under 35 U.S.C. 154(b) by 878 days.

(21) Appl. No.: 17/155,999

(22) Filed: Jan. 22, 2021

(65) Prior Publication Data

US 2021/0138229 A1 May 13, 2021

Related U.S. Application Data

(63) Continuation of application No. 15/716,168, filed on Sep. 26, 2017, now Pat. No. 10,933,182.
(Continued)

(51) Int. Cl.
*A61M 60/88* (2021.01)
*A61M 60/148* (2021.01)
(Continued)

(52) U.S. Cl.
CPC ........ *A61M 60/148* (2021.01); *A61M 60/178* (2021.01); *A61M 60/216* (2021.01);
(Continued)

(58) Field of Classification Search
None
See application file for complete search history.

(56) References Cited

U.S. PATENT DOCUMENTS 5,695,471 A 12/1997 Wampler
5,708,346 A 1/1998 Schob
(Continued)

FOREIGN PATENT DOCUMENTS

WO 2006067473 6/2006

OTHER PUBLICATIONS

Robert D. Christ et al., Chapter 13—Communications, Editor(s): Robert D. Christ, Robert L. Wernli, The ROV Manual (Second Edition), Butterworth-Heinemann, 2014, pp. 327-368, ISBN 9780080982885, https://doi.org/10.1016/B978-0-08-098288-5.00013-0, viewed on Jan. 9, 2024 (Year: 2014).*
(Continued)

*Primary Examiner* — Catherine M Voorhees
*Assistant Examiner* — James Moss
(74) *Attorney, Agent, or Firm* — Kilpatrick Townsend & Stockton LLP

(57) ABSTRACT

Systems and method for powering an implanted blood pump are disclosed herein. The system can be a mechanical circulatory support system. The mechanical circulatory support system can include an implantable blood pump. The implantable blood pump includes a DC powered pump control unit that can control the blood pump according to one or several stored instructions. The implantable blood pump includes a rectifier electrically connected to the pump control unit. The implantable rectifier can convert the AC to DC for powering the pump control unit. The system can include an external controller electrically connected to the rectifier. The external controller can provide AC electrical power to the implantable blood pump.

18 Claims, 9 Drawing Sheets

Related U.S. Application Data

(60) Provisional application No. 62/399,639, filed on Sep. 26, 2016.

(51) Int. Cl.
| | | |
|---|---|---|
| *A61M 60/178* | (2021.01) | |
| *A61M 60/216* | (2021.01) | |
| *A61M 60/411* | (2021.01) | |
| *A61M 60/422* | (2021.01) | |
| *A61M 60/82* | (2021.01) | |
| *A61M 60/822* | (2021.01) | |
| *A61M 60/863* | (2021.01) | |
| *A61M 60/871* | (2021.01) | |

(52) U.S. Cl.
CPC ........ *A61M 60/411* (2021.01); *A61M 60/422* (2021.01); *A61M 60/82* (2021.01); *A61M 60/822* (2021.01); *A61M 60/863* (2021.01); *A61M 60/871* (2021.01); *A61M 2205/8206* (2013.01); *A61M 2205/8262* (2013.01)

(56) References Cited

U.S. PATENT DOCUMENTS

| | | |
|---|---|---|
| 5,888,242 A | 3/1999 | Antaki et al. |
| 6,053,705 A | 4/2000 | Schob et al. |
| 6,071,093 A | 6/2000 | Hart |
| 6,100,618 A | 8/2000 | Schoeb et al. |
| 6,116,862 A | 9/2000 | Rau et al. |
| 6,146,325 A | 11/2000 | Lewis et al. |
| 6,186,665 B1 | 2/2001 | Maher et al. |
| 6,222,290 B1 | 4/2001 | Schoeb et al. |
| 6,234,772 B1 | 5/2001 | Wampler et al. |
| 6,249,067 B1 | 6/2001 | Schob et al. |
| 6,264,635 B1 | 7/2001 | Wampler et al. |
| 6,278,251 B1 | 8/2001 | Schob |
| 6,351,048 B1 | 2/2002 | Schob et al. |
| 6,355,998 B1 | 3/2002 | Schoeb et al. |
| 6,634,224 B1 | 10/2003 | Schob et al. |
| 6,688,861 B2 | 2/2004 | Wampler |
| 6,879,074 B2 | 4/2005 | Amrhein et al. |
| 6,991,595 B2 | 1/2006 | Burke et al. |
| 7,112,903 B1 | 9/2006 | Schob |
| 7,699,586 B2 | 4/2010 | LaRose et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,109,792 B2 | 2/2012 | Briano et al. |
| 8,152,493 B2 | 4/2012 | LaRose et al. |
| 8,323,174 B2 | 12/2012 | Jeevanandam et al. |
| 8,449,444 B2 | 5/2013 | Poirier |
| 8,506,471 B2 | 8/2013 | Bourque |
| 8,562,508 B2 | 10/2013 | Dague et al. |
| 8,597,350 B2 | 12/2013 | Rudser et al. |
| 8,652,024 B1 | 2/2014 | Yanai et al. |
| 8,657,733 B2 | 2/2014 | Ayre et al. |
| 8,668,473 B2 | 3/2014 | LaRose et al. |
| 9,308,305 B2 | 4/2016 | Chen et al. |
| 9,603,984 B2 | 3/2017 | Romero et al. |
| 9,782,527 B2 | 10/2017 | Thomas et al. |
| 2005/0071001 A1 | 3/2005 | Jarvik |
| 2007/0078293 A1 | 4/2007 | Shambaugh, Jr. et al. |
| 2008/0021394 A1 | 1/2008 | LaRose et al. |
| 2008/0021505 A1* | 1/2008 | Hastings ............ A61N 1/37518 607/9 |
| 2009/0203957 A1 | 8/2009 | LaRose et al. |
| 2010/0305692 A1 | 12/2010 | Thomas et al. |
| 2011/0160516 A1 | 6/2011 | Dague et al. |
| 2012/0046514 A1 | 2/2012 | Bourque |
| 2012/0095281 A1 | 4/2012 | Reichenbach et al. |
| 2012/0149229 A1 | 6/2012 | Kearsley et al. |
| 2013/0096364 A1* | 4/2013 | Reichenbach .......... F04D 13/06 416/174 |
| 2013/0121821 A1 | 5/2013 | Ozaki et al. |
| 2013/0127253 A1 | 5/2013 | Stark et al. |
| 2013/0170970 A1 | 7/2013 | Ozaki et al. |
| 2013/0190551 A1* | 7/2013 | Callaway ............ A61M 60/148 600/16 |
| 2013/0225909 A1 | 8/2013 | Dormanen et al. |
| 2013/0226018 A1 | 8/2013 | Kumar et al. |
| 2013/0314047 A1 | 11/2013 | Eagle et al. |
| 2014/0073838 A1* | 3/2014 | Dague ................. A61M 60/178 600/16 |
| 2014/0288352 A1* | 9/2014 | Yanai ................... A61M 60/411 600/16 |
| 2014/0296614 A1 | 10/2014 | Bolyard et al. |
| 2014/0303426 A1* | 10/2014 | Kerkhoffs ........... A61M 60/216 600/16 |
| 2015/0250936 A1 | 9/2015 | Thomas et al. |
| 2015/0290373 A1 | 10/2015 | Rudser et al. |
| 2015/0367049 A1* | 12/2015 | Chen ................... A61M 60/422 600/16 |
| 2016/0064117 A1* | 3/2016 | Romero ............... A61M 60/422 174/113 C |
| 2017/0340788 A1 | 11/2017 | Korakianitis et al. |
| 2018/0243490 A1 | 8/2018 | Kallenbach et al. |

OTHER PUBLICATIONS

Thomas Kugelstadt, Application Report The RS-485 Design Guide, https://www.ti.com/lit/an/slla272d/slla272d.pdf?ts=1704801325824&ref_url=https%253A%252F%252Fwww.google.com%252F, 2008, viewed on Jan. 9, 2024 (Year: 2008).*

* cited by examiner

continues on next page

HEART PUMP DRIVELINE POWER MODULATION

CROSS-REFERENCES TO RELATED APPLICATIONS

The present application is a Continuation of U.S. patent application Ser. No. 15/716,168 filed Sep. 26, 2017 (Allowed); which claims the benefit of U.S. Provisional Appln No. 62/399,639 filed Sep. 26, 2016, the disclosures of which are incorporated herein by reference in their entirety for all purposes.

BACKGROUND

This application relates generally to mechanical circulatory support systems, and more specifically relates to control systems, for an implantable blood pump.

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

As VAD systems continue to develop and are more widely used, the importance of reliability continues to increase. Reliability becomes particularly significant in light of the mechanical and electrical complexity of the VAD, and the interrelation and communication between the different components working with the VAD. Thus, new methods, systems, and devices that will increase the reliability of the VAD are desired.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Aspects of the present disclosure relate to systems and methods for reliably powering and communicating with an implanted blood pump. These methods can include the electrical and/or communicating connection of the implanted blood pump with a system controller via a driveline. The driveline can include a plurality of wires, and specifically a plurality of power transmission wires and at least one communication wire. The system controller, also referred to herein as the external controller, can provide AC electrical power via the driveline, and specifically via the power transmission wires of the driveline. The system controller can further send control signals to the implanted blood pump either via the power transmission wires and/or the communication wires. In the event that a wire failure and/or fault is detected, the system controller can reconfigure one or several of the plurality of wires. This reconfiguration can allow the continued powering of the implanted blood pump 14 and may also result in the maintenance of the communicating connection between the system controller and the implanted blood pump.

One aspect of the present disclosure relates to a mechanical circulatory support system. The mechanical circulatory support system can be for providing modulated AC power and control signals to an implantable pump. The system includes an implantable blood pump. The implantable blood pump includes a DC powered pump control unit that can control the blood pump according to one or several stored instructions. The implanted blood pump can include a rectifier electrically connected to the pump control unit. In some embodiments, the implantable rectifier can convert the AC to DC for powering the pump control unit. The system can include an external controller electrically connected to the rectifier. The external controller can provide AC electrical power to the implantable blood pump.

In some embodiments, the AC electrical power is driven at a frequency. In some embodiments, the frequency is selected to minimize corrosion. In some embodiments, the frequency is greater than 100 Hz, and in some embodiments, the frequency is greater than 200 Hz.

In some embodiments, the system can include a driveline electrically connecting the implantable blood pump and the external controller. This driveline can connect to the rectifier in a hermetically sealed housing.

In some embodiments, the AC electrical power is multiphase, and in some embodiments, the AC electrical power is single phase. In some embodiments, the driveline includes a plurality of power transmission wires and at least one communication wire. In some embodiments, the plurality of power transmission wires and the at least one communication wire include redundancies to allow continued powering of the implantable blood pump when at least one of the plurality of power transmission wires fails. In some embodiments, the AC electrical power changes from multiphase to single phase when the at least one of the plurality of power transmission wires fails. In some embodiments, the plurality of power transmission wires and the at least one communication wire include redundancies to allow continued powering of the implantable blood pump when at least one of the at least one communication wire fails.

One aspect of the present disclosure relates to a mechanical circulatory support system. The system includes an implantable blood pump having a DC powered pump control unit that can control the blood pump according to one or several stored instructions. The system includes an external controller electrically connected to the implantable blood pump. The external controller can provide AC electrical power to the implantable blood pump. The system can include a driveline electrically connecting the implantable blood pump and the external controller. In some embodiments, the driveline includes a plurality of power transmission wires and at least one communication wire. In some embodiments, the at least one communication wire is reconfigurable as a power transmission wire. In some embodiments, the at least one communication wire is reconfigurable as a power transmission wire by the external controller.

In some embodiments, the AC electrical power is multiphase. In some embodiments the plurality of power transmission wires includes three power transmission wires. In some embodiments the at least one communication wire includes a pair of communication wires. In some embodiments the external controller can communicate according to RS-485. In some embodiments the external controller includes a first transceiver, and the pump control unit includes a second transceiver. In some embodiments, the first transceiver and the second transceiver can operate the pair of communication wires as a differential pair. In some embodiments, the first and second transceivers can communicate via phase encoding.

In some embodiments, the external controller can provide single phase AC electrical power to the implantable blood pump. In some embodiments, the external controller can modulate the single phase AC electrical power to communicate data to the implantable blood pump via the plurality of power transmission wires of the driveline. In some embodiments, the implantable blood pump can receive data from the external controller via the plurality of power transmission wires, and the implantable blood pump can communicate data to the external controller via the at least one communication wire.

In some embodiments, the plurality of transmission wires include a pair of transmission wires, and the at least one communication wire include a single communication wire. In some embodiments the external controller can reconfigure the single communication wire as a power transmission wire. In some embodiments, the driveline does not include a wire whereby data is communicable from the implantable blood pump to the external controller when the single communication wire is reconfigured as a power transmission wire. In some embodiments, the implantable blood pump includes a magnetically levitated portion. In some embodiments, the driveline electrically connects to the implantable blood pump in a hermetically sealed housing.

One aspect of the present disclosure relates to a method of controlling an implantable pump. The method includes providing AC electrical power from an external controller to an implantable pump via a plurality of power transmission wires in a driveline including a plurality of wires. In some embodiments, the plurality of wires includes the plurality of power transmission wires and at least one communication wire. The method can include: providing a control signal from the external controller to the implantable pump via the driveline; receiving a communication at the external controller from the implantable pump via at least one communication wire in the driveline; detecting a fault in one of the plurality of wires of the driveline; and reconfiguring at least some of the plurality of wires of the driveline in response to the detected fault.

In some embodiments, the detected fault includes a short in at least one of the plurality of transmission wires. In some embodiments, reconfiguring at least some of the plurality of wires of the driveline in response to a detected fault includes reconfiguring at least one of the at least one communication wire as a power transmission wire. In some embodiments the at least one communication wire includes a pair of communication wires. In some embodiments providing the control signal includes operating the pair of communication wires as a differential pair.

In some embodiments, the method includes modulating AC electrical power to communicate data to the implantable blood pump via the plurality of power transmission wires of the driveline. In some embodiments the driveline includes a single communication wire. In some embodiments the communication is received at the external controller from the implantable pump via the single communication wire. In some embodiments, the AC electrical power is provided in single phase. In some embodiments, modulating the AC power to communicate data to the implantable blood pump via the plurality of power transmission wires of the driveline includes modulating the single phase AC electrical power to communicate data to the implantable blood pump via the plurality of power transmission wires of the driveline. In some embodiments the AC electrical power is provided in multiphase. In some embodiments, reconfiguring at least some of the plurality of wires of the driveline in response to a detected fault includes providing AC electrical power in single phase.

One aspect of the present disclosure relates to a mechanical circulatory support system for providing modulated AC power and control signals to an implantable device. The mechanical circulatory support system includes: an implantable blood pump including a DC powered pump control unit that can control the blood pump according to one or several stored instructions; an external controller electrically connected to the implantable blood pump and that can provide AC electrical power to the implantable blood pump; and a driveline electrically connecting the implantable blood pump and the external controller, which driveline includes a pair of power transmission wires, a communication wire, and a spare wire, also referred to herein as a redundant wire, and which spare wire is reconfigurable as a power transmission wire.

In some embodiments, each of the pair of power transmission wires is switchably connected to a positive terminal and a negative terminal. In some embodiments, the redundant wire is switchably connectable to the positive terminal and the negative terminal. In some embodiments, the communication wire is connected to a first capacitor that can prevent creation of a DC bias in the communication wire and the redundant wire is connected to a second capacitor that prevents creation of a DC bias in the redundant wire.

One aspect of the present disclosure relates to a mechanical circulatory support system for providing modulated AC power and control signals to an implantable device. The mechanical circulatory support system includes: an implantable blood pump including a DC powered pump control unit that can control the blood pump according to one or several stored instructions; an external controller electrically connected to the implantable blood pump and that can provide AC electrical power to the implantable blood pump; and a driveline electrically connecting the implantable blood pump and the external controller, which driveline includes a pair of power transmission wires and a pair of communication wires, at least one of which communication wires is reconfigurable as a power transmission wire.

In some embodiments, each of the pair of power transmission wires is switchably connected to a positive terminal and a negative terminal. In some embodiments, the external controller includes a first transceiver, and the pump control unit includes a second transceiver. In some embodiments, the first transceiver and the second transceiver can operate the pair of communication wires as a differential pair. In some embodiments, the pair of communication wires comprises a first communication wire and a second communication wire. In some embodiments, the first communication wire connects to the external controller via a first capacitor and the first communication wire connects to the implantable blood pump via a second capacitor.

One aspect of the present disclosure relates to a mechanical circulatory support system for providing modulated AC power and control signals to an implantable device. The mechanical circulatory support system includes: an implantable blood pump including a DC powered pump control unit that can control the blood pump according to one or several stored instructions; an external controller electrically connected to the implantable blood pump and that can provide AC electrical power to the implantable blood pump; and a driveline electrically connecting the implantable blood pump and the external controller, which driveline includes a pair of power transmission wires and a single communication wire, which communication wire is reconfigurable as a power transmission wire.

In some embodiments, each of the pair of power transmission wires is switchably connected to a positive terminal and a negative terminal. In some embodiments, the communication wire is switchably connectable to the positive terminal and the negative terminal. In some embodiments, the communication wire is connected to a capacitor that can prevent creation of a DC bias in the communication wire.

One aspect of the present disclosure relates to a method of powering an implantable pump with an external controller. The method can include receiving DC electrical power from a DC power supply at an external controller. In some embodiments, the external controller is coupled to an implantable pump via a driveline including a plurality of wires. The method can include converting the DC electrical power to AC electrical power in a transmission module of the external controller. The method can include transmitting the AC electrical power from the external controller to the implantable pump via a plurality of power transmission wires in the plurality of wires of the driveline. In some embodiments, the implantable pump can include a DC powered pump control unit.

In some embodiments, transmitting the AC electrical power from the external controller to the implantable pump includes transmitting the AC electrical power from the external controller to a rectifier of the implantable pump. In some embodiments, the AC electrical power can be single phase AC electrical power, and in some embodiments, the AC electrical power can be multiphase AC electrical power.

In some embodiments, the method includes: providing a control signal from the external controller to the implantable pump via the driveline; and receiving a communication at the external controller from the implantable pump via at least one communication wire in the driveline. In some embodiments, the at least one communication wire is one of the plurality of wires in the driveline. In some embodiments, the received communication comprises data relating to the operation of the implanted blood pump.

In some embodiments, the at least one communication wire in the driveline can be a pair of communication wires. In some embodiments, providing the control signal can include operating the pair of communication wires as a differential pair. In some embodiments, the control signal is provided according to a communication protocol to prevent the creation of a DC bias in the pair of communication wires.

In some embodiments, the method includes: detecting a fault in one of the plurality of wires of the driveline; and reconfiguring at least some of the plurality of wires of the driveline in response to the detected fault. In some embodiments, reconfiguring at least some of the plurality of wires of the driveline in response to a detected fault can include reconfiguring at least one of the at least one communication wire as a power transmission wire. In some embodiments, the AC electrical power is driven at a frequency selected to minimize corrosion. In some embodiments, the frequency is greater than 100 Hz, and in some embodiments, the frequency is greater than 200 Hz.

For a fuller understanding of the nature and advantages of the present invention, reference should be made to the ensuing detailed description and accompanying drawings.

DETAILED DESCRIPTION

Figure 1:
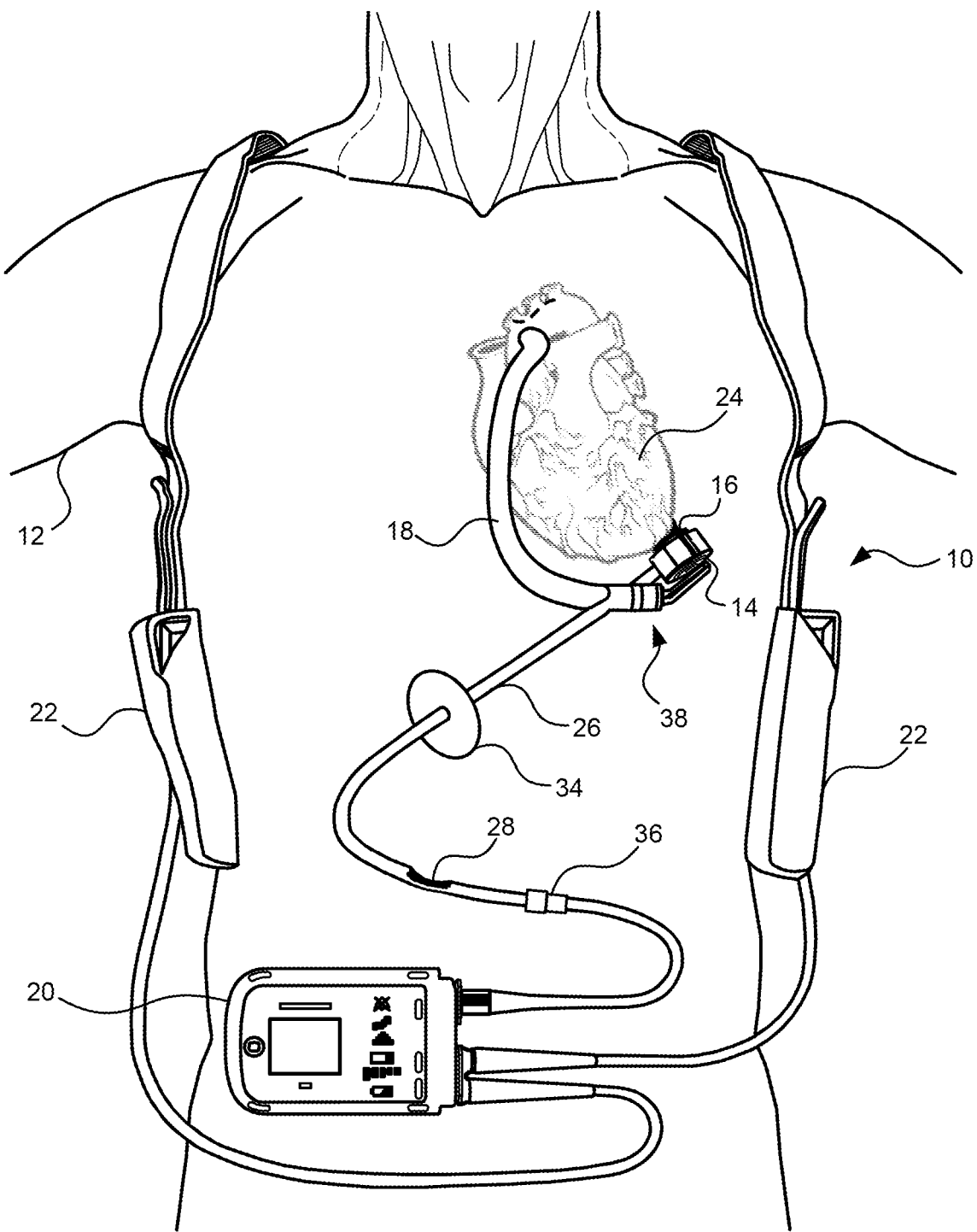
FIG. 1 is an illustration of a mechanical circulatory support system implanted in a patient's body.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Due to VAD workload, VADs can have significantly higher power requirements than other types of implantable devices such as pacemakers or other stimulators. Because of these power requirements, VADs can be externally powered by delivering power from outside of a patient's body to the VAD inside of the patient's body. In many instances, this power can be delivered via a driveline that connects to an external power source and extends into the patient's body to connect with the VAD. Some embodiments of such a driveline are disclosed in U.S. Pat. No. 9,603,984, filed on Sep. 3, 2015, and entitled "TRIPLE HELIX DRIVELINE CABLE AND METHODS OF ASSEMBLY AND USE", the entirety of which is hereby incorporated by reference herein.

While the use of a driveline to power the VAD appears to be a simple solution, there can be many difficulties with the use of such drivelines. Specifically, as the driveline extends to within the human body, portions of the driveline can be exposed to either intermittent or constant moisture. This moisture, in combination with either the transmission of power or data through the driveline can result in a high risk of corrosion, which corrosion can lead to the failure of the driveline. Further, many of these VADs include components that use DC power and/or that use only DC power. In such embodiments, DC power is provided to the VAD via the driveline, which DC power further increases the risk of corrosion. Examples of such configurations include mechanical circulatory support (MCS) systems utilizing on-board, implanted electronics. Depending on the pump, such electronics may be configured to receive DC power from the driveline and convert the power to AC inside the body. As such, a portion of the DC powered driveline is exposed to bodily fluids. Presently, this risk of corrosion is mitigated via the use of corrosion resistant materials which can be expensive and/or difficult to work with. Thus, there is a need for a mechanism, system, and/or method to reduce the risk of corrosion with a DC-configured driveline.

Some embodiments of the present disclosure address this risk of corrosion via providing AC power to the VAD and particularly to a rectifier located in a sealed container of the VAD. In such embodiments, the AC power can have a frequency selected to mitigate corrosion, and thus DC power is provided to the VAD. This risk of corrosion is further increased by the fact that the control circuitry for some VADs is DC powered. To further decrease the risk of corrosion, data can be provided through the driveline using an encoding scheme such that the transmission of data does not generate DC current in the driveline.

In addition to risk of corrosion, the use of a driveline is associated with a risk of failure of the driveline, and the resulting loss of power at the VAD. Some embodiments of the present disclosure address this risk via the inclusion of one or several "spare" wires and/or one or several wires that are reconfigurable to either power the VAD or to transmit data to or from the VAD. Some embodiments of the present disclosure relate to specific numbers of wires in the driveline, which wires can have one or several specific functions. Embodiment in which wires are reconfigurable can decrease the overall number of wires in a driveline. This decrease in the number of wires in the driveline can lead to a decrease in the size of the driveline, which decreased size of the driveline can decrease cost of the driveline, facilitate implantation of the driveline, and decrease the risk of infection caused by the driveline and/or implantation of the driveline.

Figure 2:
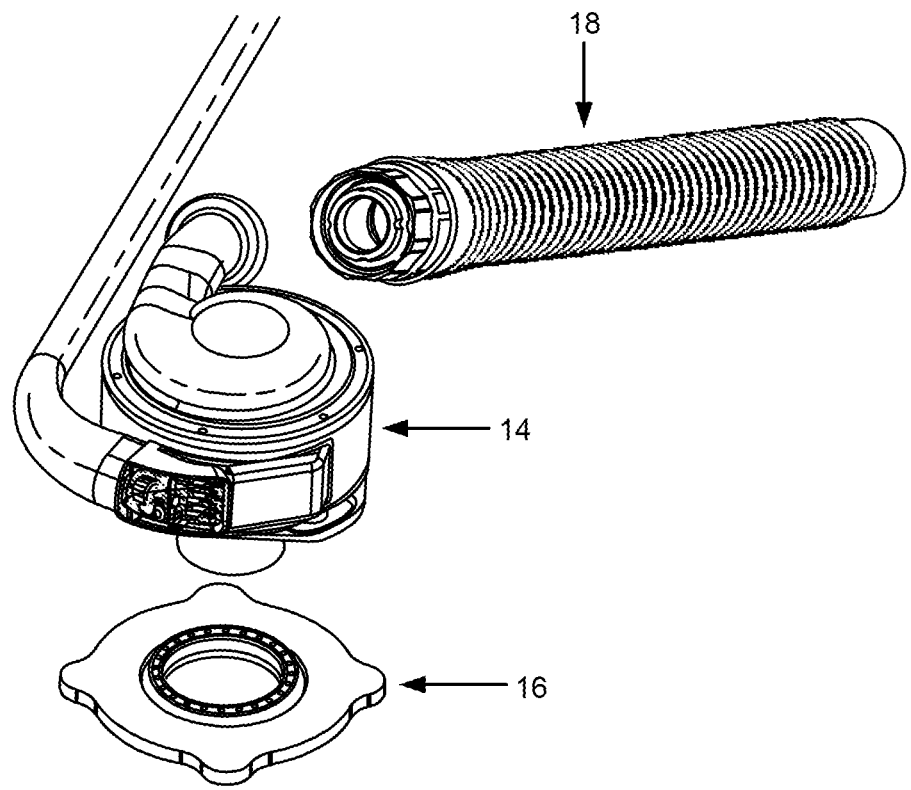
FIG. 2 is an exploded view of certain components of the circulatory support system that are implanted in a patient's body.

Referring now to the drawings, in which like reference numerals represent like parts throughout the several views, FIG. 1 is an illustration of a mechanical circulatory support system 10 implanted in a patient's body 12. The mechanical circulatory support system 10 comprises a implantable blood pump 14, ventricular cuff 16, outflow cannula 18, system controller 20, and power sources 22. The implantable blood pump 14 may comprise a VAD that is attached to an apex of the left ventricle, as illustrated, or the right ventricle, or both ventricles of the heart 24. The VAD may comprise a centrifugal (as shown) or axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471; 6,071,093; 6,116,862; 6,186,665; 6,234,772; 6,264,635; 6,688,861; 7,699,586; 7,976,271; 7,997,854; 8,007,254; 8,152,493; 8,419,609; 8,852,072; 8,652,024; 8,668,473; 8,864,643; 8,882,744; 9,068,572; 9,091,271; 9,265,870; and 9,382,908, all of which are incorporated herein by reference for all purposes in their entirety. U.S. Pat. No. 9,744,280 filed Apr. 15, 2015, and entitled Methods And Systems For LVAD Operation During Communication Losses, which is incorporated herein for all purposes, further describes an exemplary VAD with onboard electronics. With reference to FIGS. 1 and 2, the blood pump 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

FIG. 1 illustrates the mechanical circulatory support system 10 during battery 22 powered operation. A driveline 26 which exits through the patient's abdomen 28, connects the implanted blood pump 14 to the system controller 20, which monitors system 10 operation. In some embodiments, the driveline 26 exits the body via a port 34 in the skin of the patient. In some embodiments, the driveline 26 can include an external connector 36 which can be located outside of the patient's body and which can separate the driveline 26 into a first piece that connects to the implanted or implantable blood pump 14 and a second piece that connects to the system controller 20. In some embodiments, the driveline 26 can connect to the implanted blood pump 14 in a hermetically sealed housing 38.

Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety. The system may be powered by either one, two, or more batteries 22. It will be appreciated that although the system controller 20 and power source 22 are illustrated outside/external to the patient body, the driveline 26, system controller 20 and/or power source 22 may be partially or fully implantable within the patient, as separate components or integrated with the blood bump 14. Examples of such modifications are further described in U.S. Pat. Nos. 8,562,508 and 9,079,043, both of which are incorporated herein by reference for all purposes in their entirety.

Figure 3:
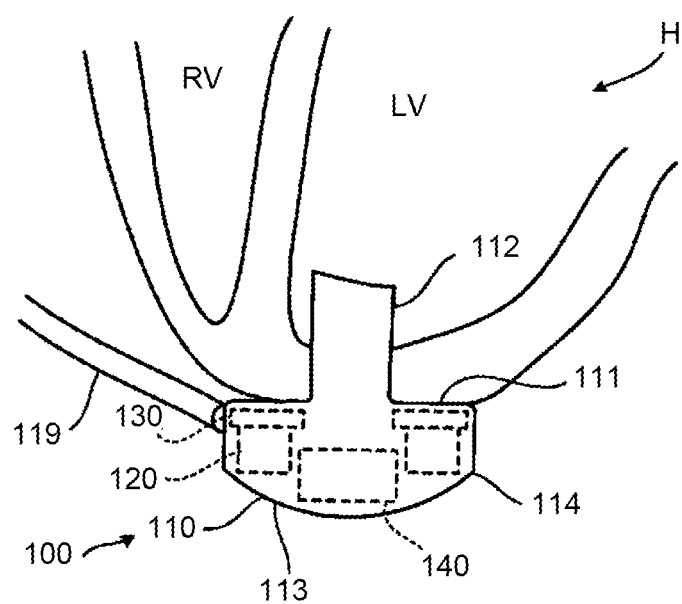
FIG. 3 is an illustration of a blood pump in an operational position implanted in a patient's body.
Figure 4:
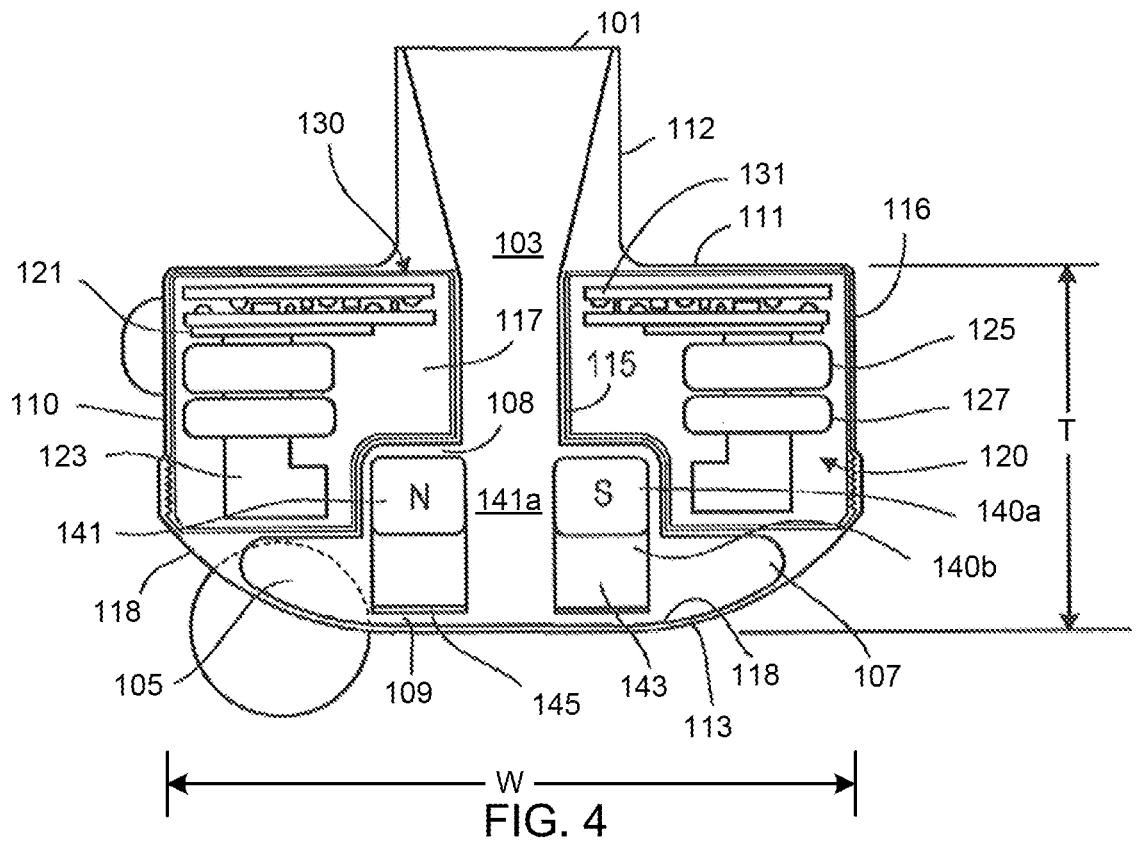
FIG. 4 is a cross-sectional view of the blood pump of FIG. 3.
Figure 5:
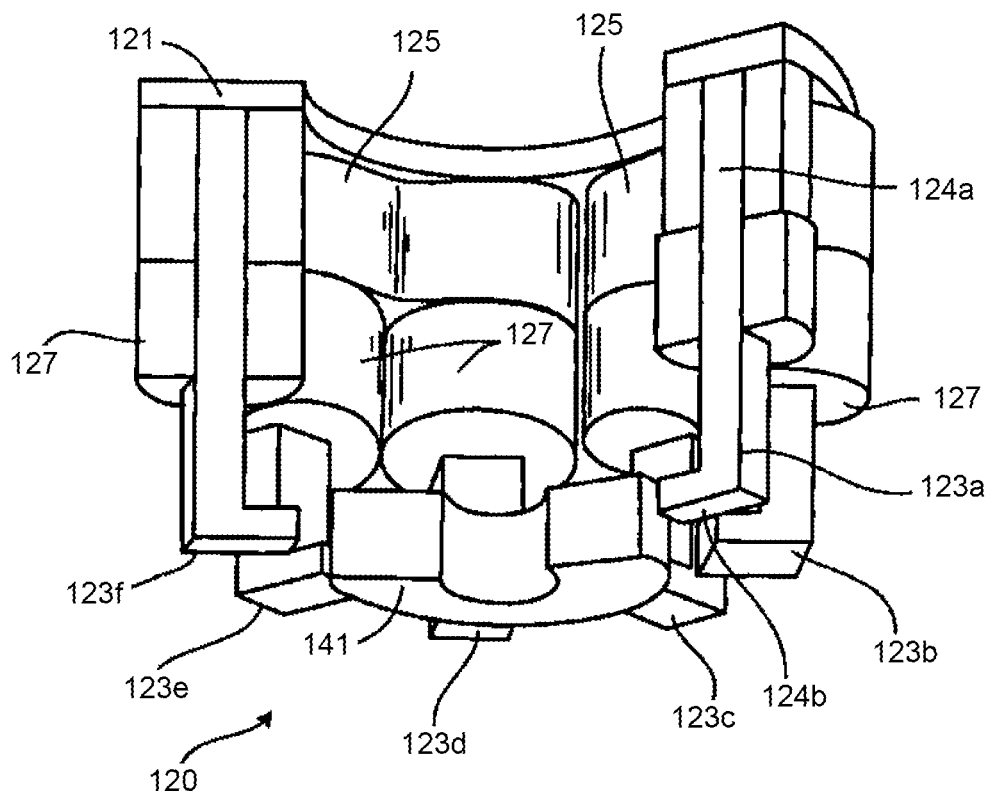
FIG. 5 is a partial cut-away perspective view of a stator of a blood pump.

With reference to FIGS. 3 to 5, a left ventricular assist blood pump 100 having a circular shaped housing 110 is implanted in a patient's body with a first face 111 of the housing 110 positioned against the patient's heart H and a second face 113 of the housing 110 facing away from the heart H. The first face 111 of the housing 110 includes an inlet cannula 112 extending into the left ventricle LV of the heart H. The second face 113 of the housing 110 has a chamfered edge 114 to avoid irritating other tissue that may come into contact with the blood pump 100, such as the patient's diaphragm. To construct the illustrated shape of the puck-shaped housing 110 in a compact form, a stator 120 and electronics 130 of the pump 100 are positioned on the inflow side of the housing toward first face 111, and a rotor 140 of the pump 100 is positioned along the second face 113. This positioning of the stator 120, electronics 130, and rotor 140 permits the edge 114 to be chamfered along the contour of the rotor 140, as illustrated in at least FIGS. 2-4, for example.

Referring to FIG. 4, the blood pump 100 includes a dividing wall 115 within the housing 110 defining a blood flow conduit 103. The blood flow conduit 103 extends from an inlet opening 101 of the inlet cannula 112 through the stator 120 to an outlet opening 105 defined by the housing 110. The rotor 140 is positioned within the blood flow conduit 103. The stator 120 is disposed circumferentially about a first portion 140a of the rotor 140, for example about a permanent magnet 141. The stator 120 is also positioned relative to the rotor 140 such that, in use, blood flows within the blood flow conduit 103 through the stator 120 before reaching the rotor 140. The permanent magnet 141 has a permanent magnetic north pole N and a permanent magnetic south pole S for combined active and passive magnetic levitation of the rotor 140 and for rotation of the rotor 140. The rotor 140 also has a second portion 140b that includes impeller blades 143. The impeller blades 143 are located within a volute 107 of the blood flow conduit such that the impeller blades 143 are located proximate to the second face 113 of the housing 110.

The puck-shaped housing 110 further includes a peripheral wall 116 that extends between the first face 111 and a removable cap 118. As illustrated, the peripheral wall 116 is formed as a hollow circular cylinder having a width W between opposing portions of the peripheral wall 116. The housing 110 also has a thickness T between the first face 111 and the second face 113 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 116 encloses an internal compartment 117 that surrounds the dividing wall 115 and the blood flow conduit 103, with the stator 120 and the electronics 130 disposed in the internal compartment 117 about the dividing wall 115. The removable cap 118 includes the second face 113, the chamfered edge 114, and defines the outlet opening 105. The cap 118 can be threadedly engaged with the peripheral wall 116 to seal the cap 118 in engagement with the peripheral wall 116. The cap 118 includes an inner surface 118a of the cap 118 that defines the volute 107 that is in fluid communication with the outlet opening 105.

Within the internal compartment 117, the electronics 130, which can be DC powered, and specifically which can be transcutaneously DC powered, are positioned adjacent to the first face 111 and the stator 120 is positioned adjacent to the electronics 130 on an opposite side of the electronics 130 from the first face 111. The electronics 130, also referred to herein as a pump control unit, include circuit boards 131 and various components carried on the circuit boards 131 to control the operation of the pump 100 (e.g., magnetic levitation and/or drive of the rotor) by controlling the electrical supply to the stator 120. In some embodiments, the electronics 130 can control the operation of all or portions of the implanted blood pump 14 according to one or several stored instructions and/or stored code. In some embodiments, for example, the electronics 130 can be configured to generate a first set of signals configured to control the levitation of the rotor and a second set of signals configured to control the drive of the rotor. In some embodiments, the electronics 130 can be further configured to provide AC power to the pump 100, and specifically the electronics 130 can be further configured to convert the received DC input to AC and to provide the AC to the pump 100.

In some embodiment, the pump control unit 130 can be DC powered and can be electrically connected to the driveline 26 via a rectifier which can be a component of the implanted blood pump 14, and can be implanted with the implanted blood pump 14. Thus, in some embodiments, the pump control unit 130 can be electrically connected to the rectifier, which rectifier can be electrically connected to the driveline 26, and specifically can be electrically connected to the driveline 26 in a hermetically sealed housing. In some embodiments, for example, the system controller 20, also referred to herein as the external controller 20, can provide electrical power to the implanted blood pump 14 via, for example, the driveline 26. In some embodiments, the external controller can provide AC electrical power to the implanted blood pump 14 via the driveline, which AC electrical power can be converted to DC electrical power by the rectifier, which rectifier can then provide DC power to the electronics 130.

The housing 110 is configured to receive the circuit boards 131 within the internal compartment 117 generally parallel to the first face 111 for efficient use of the space within the internal compartment 117. The circuit boards also extend radially-inward towards the dividing wall 115 and radially-outward towards the peripheral wall 116. For example, the internal compartment 117 is generally sized no larger than necessary to accommodate the circuit boards 131, and space for heat dissipation, material expansion, potting materials, and/or other elements used in installing the circuit boards 131. Thus, the external shape of the housing 110 proximate the first face 111 generally fits the shape of the circuits boards 131 closely to provide external dimensions that are not much greater than the dimensions of the circuit boards 131.

With continued reference to FIGS. 4 and 5, the stator 120 includes a back iron 121 and pole pieces 123a-123f arranged at intervals around the dividing wall 115. The back iron 121 extends around the dividing wall 115 and is formed as a generally flat disc of a ferromagnetic material, such as steel, in order to conduct magnetic flux. The back iron 121 is arranged beside the control electronics 130 and provides a base for the pole pieces 123a-123f.

Each of the pole piece 123a-123f is L-shaped and has a drive coil 125 for generating an electromagnetic field to rotate the rotor 140. For example, the pole piece 123a has a first leg 124a that contacts the back iron 121 and extends from the back iron 121 towards the second face 113. The pole piece 123a may also have a second leg 124b that extends from the first leg 124a through an opening of a circuit board 131 towards the dividing wall 115 proximate the location of the permanent magnet 141 of the rotor 140. In an aspect, each of the second legs 124b of the pole pieces 123a-123f is sticking through an opening of the circuit board 131. In an aspect, each of the first legs 124a of the pole pieces 123a-123f is sticking through an opening of the circuit board 131. In an aspect, the openings of the circuit board are enclosing the first legs 124a of the pole pieces 123a-123f.

In a general aspect, the implantable blood pump 100 may include a Hall sensor that may provide an output voltage, which is directly proportional to a strength of a magnetic field that is located in between at least one of the pole pieces 123a-123f and the permanent magnet 141, and the output voltage may provide feedback to the control electronics 130 of the pump 100 to determine if the rotor 140 and/or the permanent magnet 141 is not at its intended position for the operation of the pump 100. For example, a position of the rotor 140 and/or the permanent magnet 141 may be adjusted, e.g. the rotor 140 or the permanent magnet 141 may be pushed or pulled towards a center of the blood flow conduit 103 or towards a center of the stator 120.

Each of the pole pieces 123a-123f also has a levitation coil 127 for generating an electromagnetic field to control the radial position of the rotor 140. Each of the drive coils 125 and the levitation coils 127 includes multiple windings of a conductor around the pole pieces 123a-123f. Particularly, each of the drive coils 125 is wound around two adjacent ones of the pole pieces 123, such as pole pieces 123d and 123e, and each levitation coil 127 is wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the stator 120 are arranged in opposing pairs and are controlled to drive the rotor and to radially levitate the rotor 140 by generating electromagnetic fields that interact with the permanent magnetic poles S and N of the permanent magnet 141. Because the stator 120 includes both the drive coils 125 and the levitation coils 127, only a single stator is needed to levitate the rotor 140 using only passive and active magnetic forces. The permanent magnet 141 in this configuration has only one magnetic moment and is formed from a monolithic permanent magnetic body 141. For example, the stator 120 can be controlled as discussed in U.S. Pat. No. 6,351,048, the entire contents of which are incorporated herein by reference for all purposes. The control electronics 130 and the stator 120 receive electrical power from a remote power supply via a cable 119 (FIG. 3). Further related patents, namely U.S. Pat. Nos. 5,708,346, 6,053,705, 6,100,618, 6,222,290, 6,249,067, 6,278,251, 6,351,048, 6,355,998, 6,634,224, 6,879,074, and 7,112,903, all of which are incorporated herein by reference for all purposes in their entirety.

The rotor 140 is arranged within the housing 110 such that its permanent magnet 141 is located upstream of impeller blades in a location closer to the inlet opening 101. The permanent magnet 141 is received within the blood flow conduit 103 proximate the second legs 124b of the pole pieces 123 to provide the passive axial centering force though interaction of the permanent magnet 141 and ferromagnetic material of the pole pieces 123. The permanent magnet 141 of the rotor 140 and the dividing wall 115 form a gap 108 between the permanent magnet 141 and the dividing wall 115 when the rotor 140 is centered within the dividing wall 115. The gap 108 may be from about 0.2 millimeters to about 2 millimeters. For example, the gap 108 is approximately 1 millimeter. The north permanent magnetic pole N and the south permanent magnetic pole S of the permanent magnet 141 provide a permanent magnetic attractive force between the rotor 140 and the stator 120 that acts as a passive axial centering force that tends to maintain the rotor 140 generally centered within the stator 120 and tends to resist the rotor 140 from moving towards the first face 111 or towards the second face 113. When the gap 108 is smaller, the magnetic attractive force between the permanent magnet 141 and the stator 120 is greater, and the gap 108 is sized to allow the permanent magnet 141 to provide the passive magnetic axial centering force having a magnitude that is adequate to limit the rotor 140 from contacting the dividing wall 115 or the inner surface 118a of the cap 118. The rotor 140 also includes a shroud 145 that covers the ends of the impeller blades 143 facing the second face 113 that assists in directing blood flow into the volute 107. The shroud 145 and the inner surface 118a of the cap 118 form a gap 109 between the shroud 145 and the inner surface 118a when the rotor 140 is levitated by the stator 120. The gap 109 is from about 0.2 millimeters to about 2 millimeters. For example, the gap 109 is approximately 1 millimeter.

As blood flows through the blood flow conduit 103, blood flows through a central aperture 141a formed through the permanent magnet 141. Blood also flows through the gap 108 between the rotor 140 and the dividing wall 115 and through the gap 109 between the shroud 145 and the inner surface 108a of the cap 118. The gaps 108 and 109 are large enough to allow adequate blood flow to limit clot formation that may occur if the blood is allowed to become stagnant. The gaps 108 and 109 are also large enough to limit pressure forces on the blood cells such that the blood is not damaged when flowing through the pump 100. As a result of the size of the gaps 108 and 109 limiting pressure forces on the blood cells, the gaps 108 and 109 are too large to provide a meaningful hydrodynamic suspension effect. That is to say, the blood does not act as a bearing within the gaps 108 and 109, and the rotor is only magnetically-levitated. In various embodiments, the gaps 108 and 109 are sized and dimensioned so the blood flowing through the gaps forms a film that provides a hydrodynamic suspension effect. In this manner, the rotor can be suspended by magnetic forces, hydrodynamic forces, or both.

Because the rotor 140 is radially suspended by active control of the levitation coils 127 as discussed above, and because the rotor 140 is axially suspended by passive interaction of the permanent magnet 141 and the stator 120, no rotor levitation components are needed proximate the second face 113. The incorporation of all the components for rotor levitation in the stator 120 (i.e., the levitation coils 127 and the pole pieces 123) allows the cap 118 to be contoured to the shape of the impeller blades 143 and the volute 107. Additionally, incorporation of all the rotor levitation components in the stator 120 eliminates the need for electrical connectors extending from the compartment 117 to the cap 118, which allows the cap to be easily installed and/or removed and eliminates potential sources of pump failure.

In use, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. For example, the Hall sensor may sense a current position of the rotor 140 and/or the permanent magnet 141, wherein the output voltage of the Hall sensor may be used to selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into pump 100 through the inlet opening 101. As blood is drawn into the blood pump by rotation of the impeller blades 143 of the rotor 140, the blood flows through the inlet opening 101 and flows through the control electronics 130 and the stator 120 toward the rotor 140. Blood flows through the aperture 141a of the permanent magnet 141 and between the impeller blades 143, the shroud 145, and the permanent magnet 141, and into the volute 107. Blood also flows around the rotor 140, through the gap 108 and through the gap 109 between the shroud 145 and the inner surface 118a of the cap 118. The blood exits the volute 107 through the outlet opening 105, which may be coupled to an outflow cannula.

Figure 6:
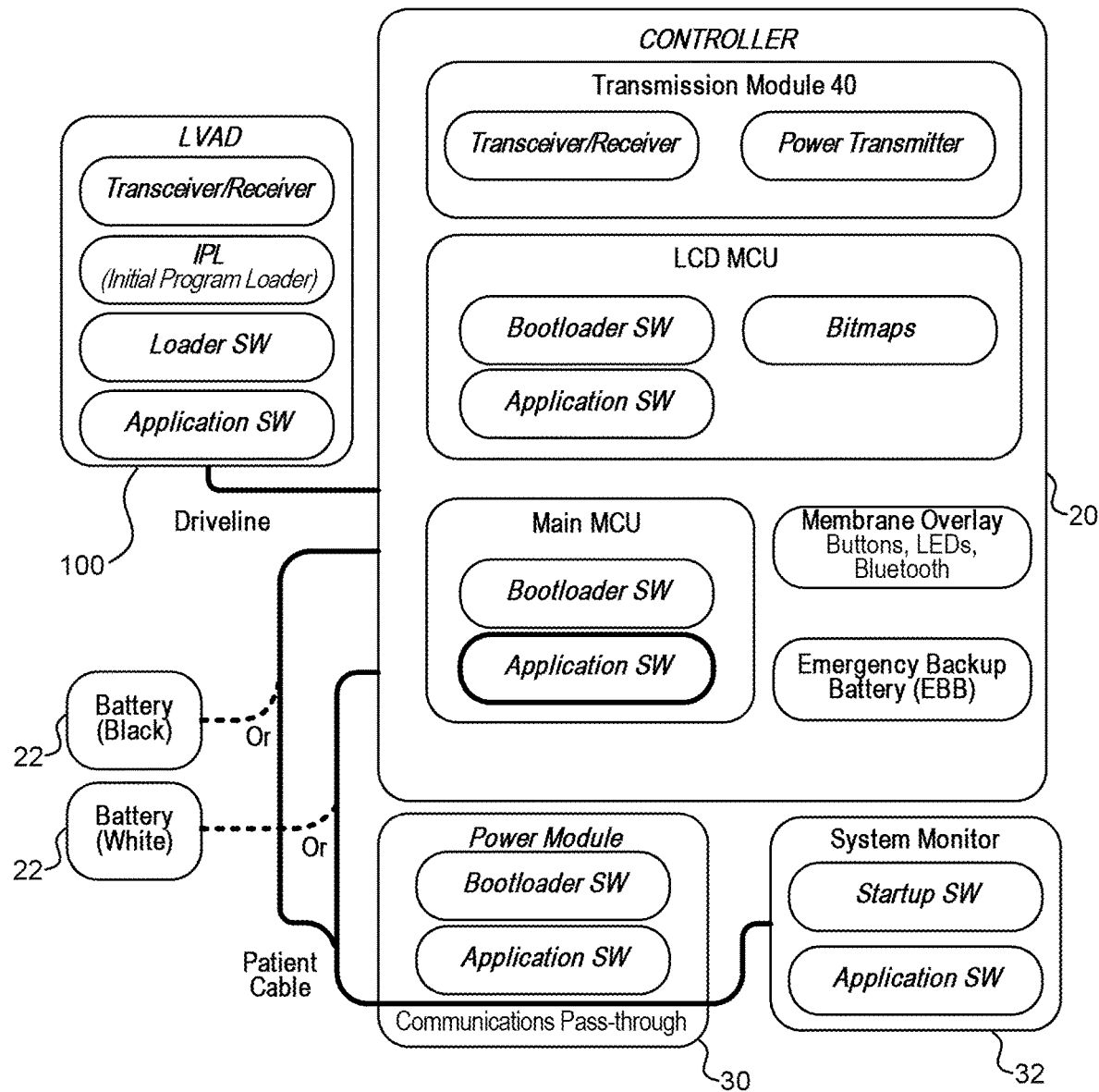
FIG. 6 is a schematic diagram of an overall communication architecture of the mechanical support system of FIG. 1.

FIG. 6 is a schematic diagram of an overall communication architecture of the mechanical support system of FIG. 1. A driveline couples the implanted blood pump 100 to the system controller 20, which monitors system operation via various software applications. The blood pump 100 itself also includes several software applications that are executable by the on board electronics 130 (e.g., processors) for various functions, such as to control radial levitation and/or drive of the rotor of the pump 100 during operation. The system controller 20 may in turn be coupled to batteries 22 or a power module 30 that can connect to an AC electrical outlet. The system controller 20 may also include an emergency backup battery (EBB) to power the system (e.g., when the batteries 22 are depleted) and a membrane overlay, including bluetooth capabilities for wireless data communication.

In some embodiments, the system controller 20 can include a transmission module 40 that can include a transceiver, transmitter, and/or receiver. As used herein, the transceiver, transmitter, and/or receiver of the system controller 20 can be respectively referred to as the first transceiver, the first transmitter, and/or the first receiver. In some embodiments, the transceiver, transmitter, and/or receiver can send one or several signals comprising data to, and/or receive signal comprising data from the implanted blood pump 14, and specifically to a transceiver, transmitter, and/or receiver of the implanted blood pump 14 via the driveline 26. As used herein, the transceiver, transmitter, and/or receiver of the implanted blood pump 14 can be respectively referred to as the second transceiver, the second transmitter, and/or the second receiver.

In some embodiments, the transmission module 40 can include a power transmitter configured to provide electrical power to the implanted blood pump 14 via, for example, the driveline 26. In some embodiments, the system controller 20 can control one or several attributes of the electrical power provided to the implanted blood pump 14. In some embodiments, for example, the electrical power provided to the implanted blood pump 14 can comprise AC electrical power. In some embodiments, the system controller 20 can control the phase of the AC electrical power, the frequency of the AC electrical power, and/or the like. In some embodiments, the AC electrical power can be single phase AC electrical power or multi-phase AC electrical power. In some embodiments, the AC electrical power can be dual phase AC electrical power. In some embodiments, the system controller 20 can provide AC electrical power with a frequency to prevent and/or minimize electrolysis and/or corrosion of all or portions of the implanted blood pump 14, the external controller 20, and/or the driveline 26. In some embodiments, for example, the frequency of the provided AC electrical power can be set to a frequency greater than or equal to approximately 100 Hz, 200 Hz, 500 Hz, 1000 Hz, and/or any other or intermediate frequency.

An external computer having a system monitor 32 that is configurable by an operator, such as clinician or patient, may further be coupled to the circulatory support system for configuring the system controller 20, implanted blood pump 100, and/or patient parameters, updating software on the system controller 20 and/or implanted blood pump 100, monitoring system operation, and/or as a conduit for system inputs or outputs.

In some embodiments, the software applications of the blood pump 100 can include, for example, an initial program loader (IPL), loader software, and/or application software. In some embodiments, the IPL can be configured to select and load one or several software applications corresponding to one or several modes of operation of the blood pump 100. In some embodiments, these one or several modes of operation of the blood pump 100 can include an operation mode, a test mode, a fault mode, or the like. The selecting and loading of one or several software applications corresponding to one or several modes of operation of the blood pump 100 can include, for example, selecting and loading one or several of the loader software and/or the application software. In some embodiments, the IPL can include information relating to one or several failsafe and/or fault protocols that can be used by the blood pump 100. Some of these failsafe and/or fault protocols will be discussed at length below.

The loader software, can, in some embodiments, be configured to direct the operation of the blood pump 100 during the loading of one or several software applications onto the blood pump 100. These one or several software applications can include, for example, one or several application softwares, one or several IPL applications, or the like. In some embodiments, the loader software can prescribe one or several processes for updating and/or loading one or several software applications onto the blood pump 100. These processes and associated failsafes will be discussed in greater details below.

The application software can include one or several parameters for directing the pumping operation of the blood pump 100. In some embodiments, the application software can comprise one of a clinical application software which can be configured to control the operation of the blood pump 100 when implanted in a patient, and in some embodiments, the application software can comprise a production software that can be configured to control the operation of the blood pump 100 during production and/or testing of the blood pump 100.

In some embodiments, these parameters can specify a control or control regimen for the position and/or motion of the rotor 140. For example, these parameters can specify the aspects of the levitation control and/or rotation control of the rotor 140.

In some embodiments, the parameters of the application software can specify, for example a desired performance of the blood pump 100 and/or one or several desired performance parameters, such as, for example, a desired pump speed, and desired pumped flow rate, a pulse generation, or the like. In some embodiments, these parameters can be actively used to control the operation of the blood pump 100, and in some embodiments these parameters can be stored during normal operation of the blood pump 100 and used as part of one or several failsafe and/or fault protocols. In some embodiments, the parameters of the application software can specify the generation and/or collection of data from the blood pump 100 and/or interfacing of the blood pump 100 to other components of the mechanical circulatory support system 10.

In some embodiments, the application software can comprises a first application software containing parameters relating to the current operation of the blood pump, and in some embodiments, the application software can comprise a second application software containing parameters unrelated to the current operation of the blood pump 100. In one embodiment, for example, the blood pump 100 can comprise the second application software as a backup to the first application software. In some embodiments, the first application software can be identical to the second application software, and in some embodiments, the first application can be different than the second application software.

Figure 7:
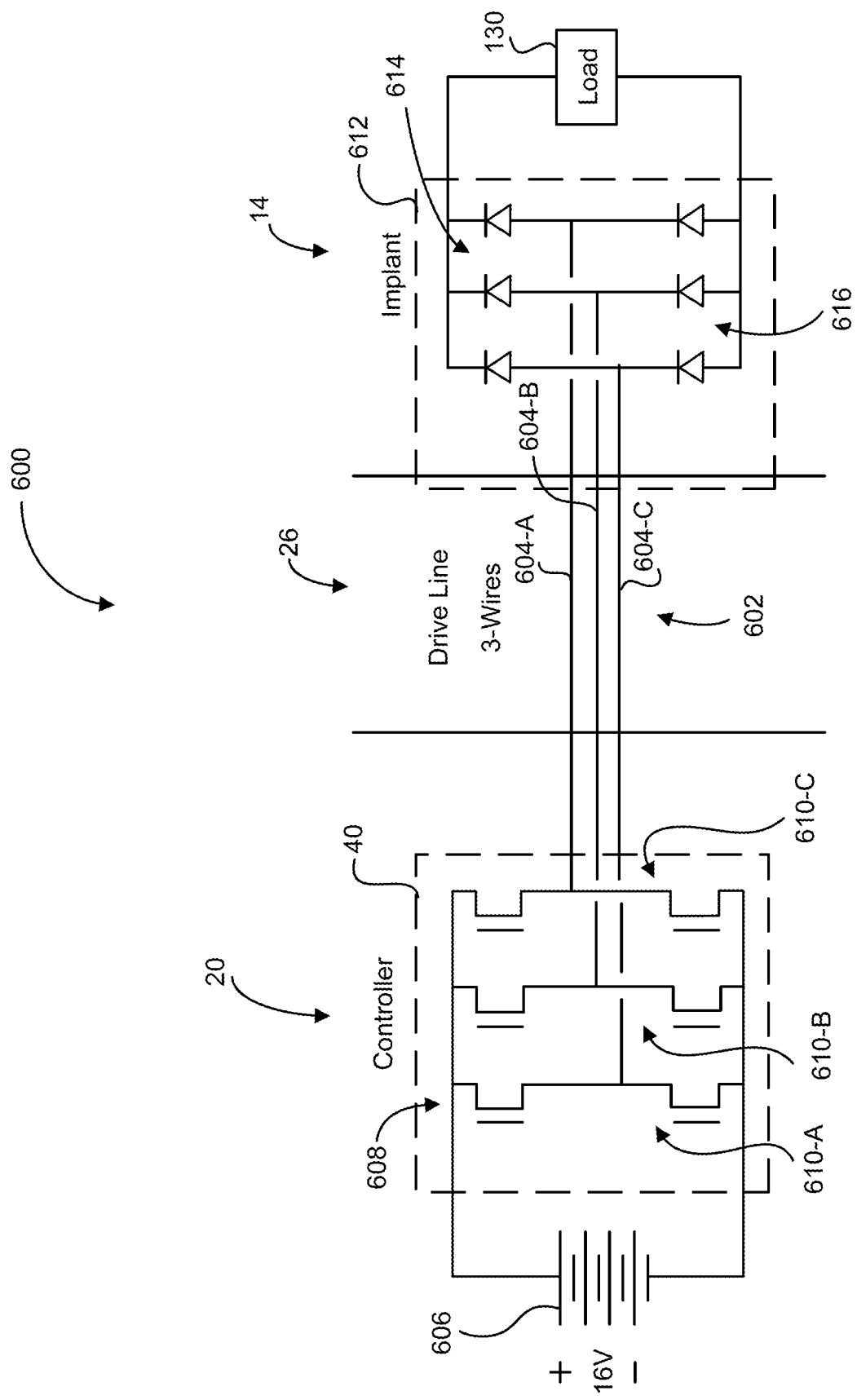
FIG. 7 is a schematic illustration of an embodiment of a connection between the implanted blood pump and the system controller via a three-wire driveline.

With reference to FIGS. 7-10 schematics of embodiments of connections between the implanted blood pump 14 and the system controller 20 are shown. One embodiment of a three-wire connection between the implanted blood pump 14 and the controller 20 is shown in FIG. 7. In some embodiments, and as seen in FIG. 7, the driveline 26 comprises a plurality of wires 602, and specifically a plurality of power transmission wires 604. In the specific embodiment depicted in FIG. 7, the driveline 26 includes three power transmission wires and specifically a first power transmission wire 604-A, a second power transmission wire 604-B, and a third power transmission wire 604-C. The system controller 20 depicted in FIG. 7 includes a power supply 606. In some embodiments, the power supply 606 can supply DC electrical power, and in some embodiments, the power supply 606 can supply AC electrical power.

In some embodiments, the system controller 20 can include an array of switches 608 that can be part of the transmission module 40 of the system controller 20. In some embodiments, the switches in the array of switches can be field-effect transistors (FETs) that can be arranged in a FET bridge. The switches in the array of switches 608 can be controlled by, for example, a processor associated with the transmission module 40 and/or the system controller 20 to generate AC electrical power from the DC electrical power of the power supply 606. The switches in the array of switches 608 are arranged into switch pairs 610 that each comprise two switches. In some embodiments, each of the power transmission wires 604 of the driveline 26 can be connected to one of the switch pairs 610 such that each of the power transmission wire 604 can be electrically connected to a positive terminal of the power supply 606 by the closing of one of the switches of its switch pair 610 and each of the power transmission wires 604 can be electrically connected to a negative terminal of the power supply 606 by the closing of the other of the switches of it switch pair 610.

In some embodiments, the switches in the array of switches 608 can be controllably opened and closed to generate AC electrical power that can be provided to the implanted blood pump 14 via driveline 26. The driveline 26 can electrically connect to a rectifier 614 inside of a hermetically sealed housing 612. The rectifier 614 can be, for example, electrically connected to a load such as the other portions of the implanted blood pump 14 and specifically the electronics 130 of the implanted blood pump 14. In some embodiments, the rectifier 614 can comprise a plurality of components that control the flow direction of current exiting the rectifier which plurality of components can, in some embodiments, comprise a plurality of diodes 616.

In some embodiments, the system controller 20, and specifically the transmission module 40, the power transmitter of the transmission module 40, and/or the transceiver/receiver of the transmission module 40 can provide one or several control signals to the implanted blood pump 14 and/or can provide data to the implanted blood pump 14. In some embodiments, this can include providing power-line communication. In some embodiments, this can be achieved by, for example, the super positioning of a low-energy information signal on the power wave of the AC electrical power. In some embodiments, for example, the data signal can have a frequency that is significantly different from the frequency of the AC electrical power. In some embodiments, for example, in which the frequency of the AC electrical power is approximately 100 Hz or 200 Hz, the data signal can have a frequency of at least approximately 1 kHz, 2 kHz, 3 kHz, 4 kHz, 5 kHz, 6 kHz, 7 kHz, 8 kHz, 9 kHz, 10 kHz, and/or any other desired frequency.

In some embodiments, the system controller 20 and specifically the transmission module 40 can provide AC electrical power in single phase, dual phase (two-phase), three-phase, and/or multi-phase. In the embodiment depicted in FIG. 7, the AC electrical power can be provided in single phase or three phase. In some embodiments, the system controller 20 can be configured to provide single phase AC electrical power and to modulate the single phase AC electrical power to communicate data to the implanted blood pump 14 via the plurality of power transmission wires 604 of the driveline 26.

In some embodiments, the system controller 20 can be configured to monitor the status of the plurality of wires 602 and specifically of the plurality of transmission wire 604 to determine whether any of the plurality of wires 602 and specifically any of the plurality of transmission wire 604 fails and/or faults. In some embodiments, such a failure and/or fault can include a shorting of one or several of the plurality of wires 602 and specifically shorting of one or several of the plurality of transmission wires 604. In the event that a short is detected, the system controller 20 can determine whether at least two of the power transmission wires 604 have not failed and/or faulted. If at least two of the power transmission wires 604 have not failed and/or vaulted, then the system controller 20 can continue providing AC electrical power via those identified at least two power transmission wires 604. In some embodiments, this can include changing the phase of the AC electrical power such as, for example, decreasing the phase of the AC electrical power. Specifically, and with respect to FIG. 7, in the event that one of the power transmission wire 604 fails and/or faults, the system controller can discontinue providing three phase AC electrical power and can begin providing single phase AC electrical power.

Figure 8:
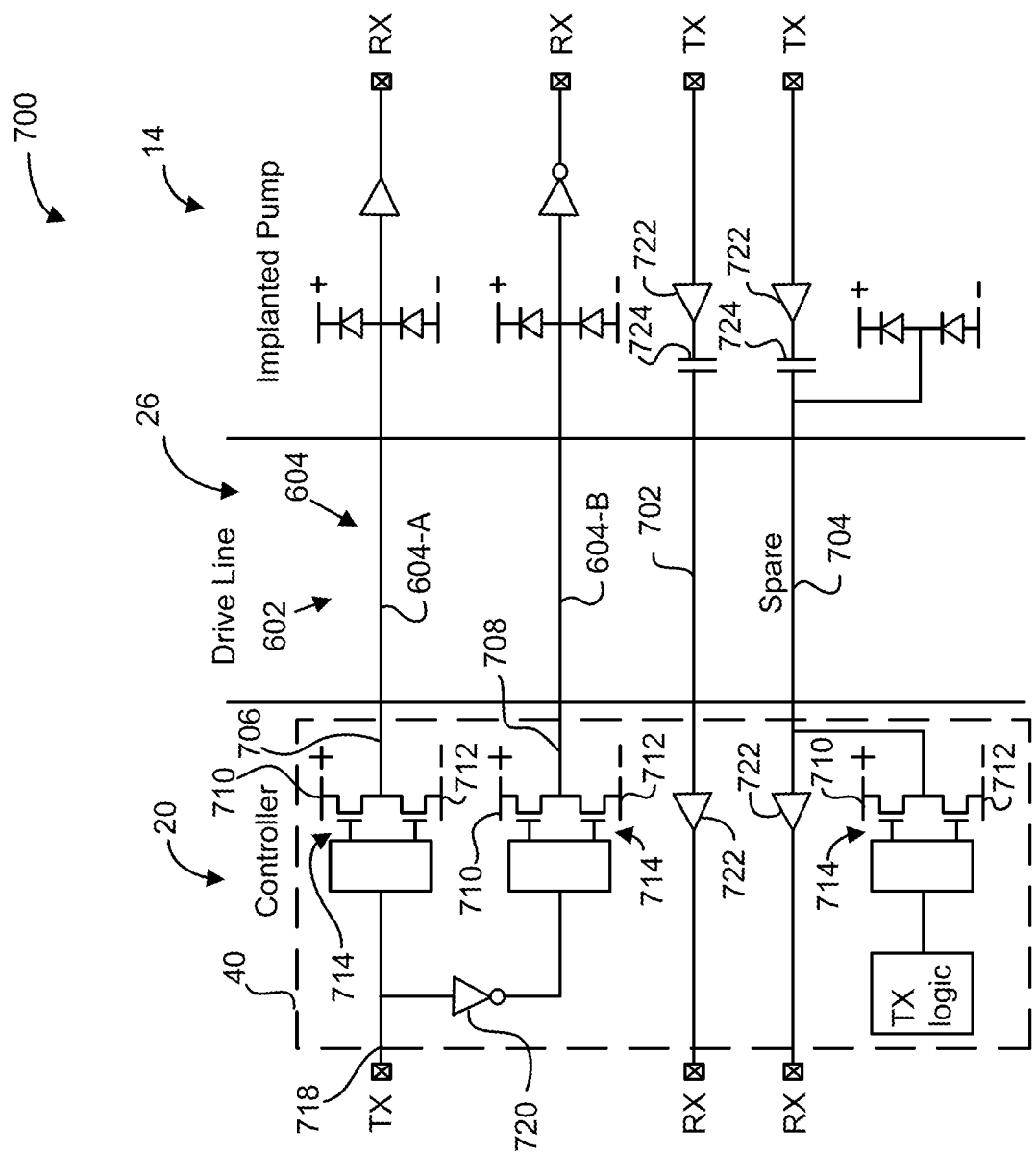
FIG. 8 is a system for connecting between the system controller and the implanted pump.

With reference now to FIG. 8, an embodiment of a system 700 for connecting between the system controller 20 and the implanted pump 14 with a four wire driveline 26 is shown. As seen in FIG. 8, the driveline 26 includes a plurality of wires 602, and specifically four wires. This plurality of wires 602 includes a plurality of power transmission wires 604, a communication wire 702, and a spare wire 704, also referred to herein as a redundant wire 704, that can be configurable as either a power transmission wire 604 or as a communication wire 702. In some embodiments, the plurality of power transmission wires 604 and at least one communication wire can include redundancies and/or can be reconfigured to redundantly transmit power and/or data to allow continued powering of the implantable blood pump in the event that at least one of the plurality of wires such as at least one of the plurality of power transmission wires and/or of the communication wires fails.

As seen in FIG. 8, the system controller 20 includes the transmission module 40. The transmission module 40 can include a first output 706 and a second output 708. The first output 706 can connect to the first power transmission wire 604-A and the second output 708 can connect to the second power transmission wire 604-B. As further seen, each of the first output 706 and the second output 708 can be selectively connected to a positive terminal 710, also referred to herein as a positive voltage source, and/or a negative terminal 712, also referred to herein as a negative voltage source, via a plurality of switches 714 which can be, for example, one or several FETs. In some embodiments, the control of these plurality of switches 714 can result in one or both of the first output 706 and the second output 708 having a positive or negative voltage. In some embodiments, the plurality of switches 714 controlling the voltage of the first output 706 can be controlled according to a control signal received via connection 718. In some embodiments, and as seen in FIG. 8, the plurality of switches 714 controlling the voltage of the second output can connect to connection 718 via the logic inverter 720 such that the switching of the plurality of switches 714 controlling the voltage of the second output 708 is opposite to the switching of the plurality of switches 714 controlling the voltage of the first output 706. Thus, when the first output 706 is connected to the positive voltage source 710, the second output 708 is connected to the negative voltage source 712. The controlling of the switching such that the voltage of the second output 708 is opposite to the voltage of the first output 706 allows the creation of AC electrical current in the first and second output 706, 708.

The communication wire 702 shown in FIG. 8 includes two direction flow elements, and specifically two diodes 722, and a capacitor 724. In some embodiments, the direction flow elements can be positioned and configured so as to allow the travel of current from the implanted blood pump 14 to the system controller 20. Thus, in some embodiments and specifically in the embodiment depicted in FIG. 8, the communication wire 702 can be configured to transmit data from the implanted blood pump 14 to the system controller 20.

As further seen in FIG. 8, the redundant wire 704 is likewise switchably connectable to one or both of the positive voltage source 710 and the negative voltage source 712 via a plurality of switches 714. In some embodiments, this switchable connection to the positive voltage source 710 and the negative voltage source 712 can allow the reconfiguring of the redundant wire 704 as a power transmission wire 604 in the event of the failure and/or fault of one of the power transmission wires 604. In some embodiments, the spare wire includes two direction flow elements, and specifically two diodes 722, and a capacitor 724 in the same configuration as the diodes 722 and capacitor 724 of the communication wire 702. Thus, in the event of the failure of the communication wire 702, the redundant wire 704 can be reconfigured as the communication wire 702.

In some embodiments, and as depicted in FIG. 8, AC electrical power can be provided via the power transmission wires 604 and data can be communicated from the implanted blood pump 14 to the system controller 20 via the communication wire 702. In some such embodiments, data can also be communicated from the system controller 20 to the implanted blood pump 14 via the power transmission wires 604, and specifically by modulating the provided AC electrical power to include data and/or by overlaying a data signal onto the AC electrical power as discussed above.

In some embodiments, the system 700 can be a mechanical circulatory support system for providing modulated AC power and control signals to the implantable blood pump 14. This implantable blood pump can include: a DC powered pump control unit 130 that can control the implantable blood pump 14 according to one or several stored instructions; a rectifier 614 that can be electrically connected to the pump control unit 130, which implantable rectifier 614 is can convert all or portions of the received AC to DC for powering the pump control unit 130. The system can include an external controller 20 that can be electrically connected to the rectifier 614 via, for example, the driveline 602. The external controller 20 can provide AC electrical power to the implantable blood pump 14.

The driveline 602 can include a pair of power transmission wires 604, a communication wire 702, and a spare wire 704, also referred to herein as a redundant wire 704. Each of the pair of power transmission wires 604 can connect to an output 706, 708 of the external controller 20. Specifically, the first output 706 can connect to the first power transmission wire 604-A and the second output 708 can connect to the second power transmission wire 604-B. Each of these outputs 706, 708 can be switchably connected to the positive voltage source 710 and/or the negative voltage source 712, via the plurality of switches 714, which plurality of switches 714 can be controlled to generate AC electrical power in the power transmission wires 604 of a desired frequency.

The communication wire 702 can connect to a transceiver in the transmission module 40 and/or to a transceiver and/or receiver in the implantable blood pump 14. The redundant wire 704 can be configured for use as a communication wire by connecting the redundant wire 704 to a transceiver in the transmission module 40 and/or to a transceiver and/or receiver in the implantable blood pump 14, and the redundant wire 704 can be configured for use as a power transmission wire 604 by switchably connecting the spare wire 704 to the positive voltage source 710 and/or the negative voltage source 712, via the plurality of switches 714.

Figure 9:
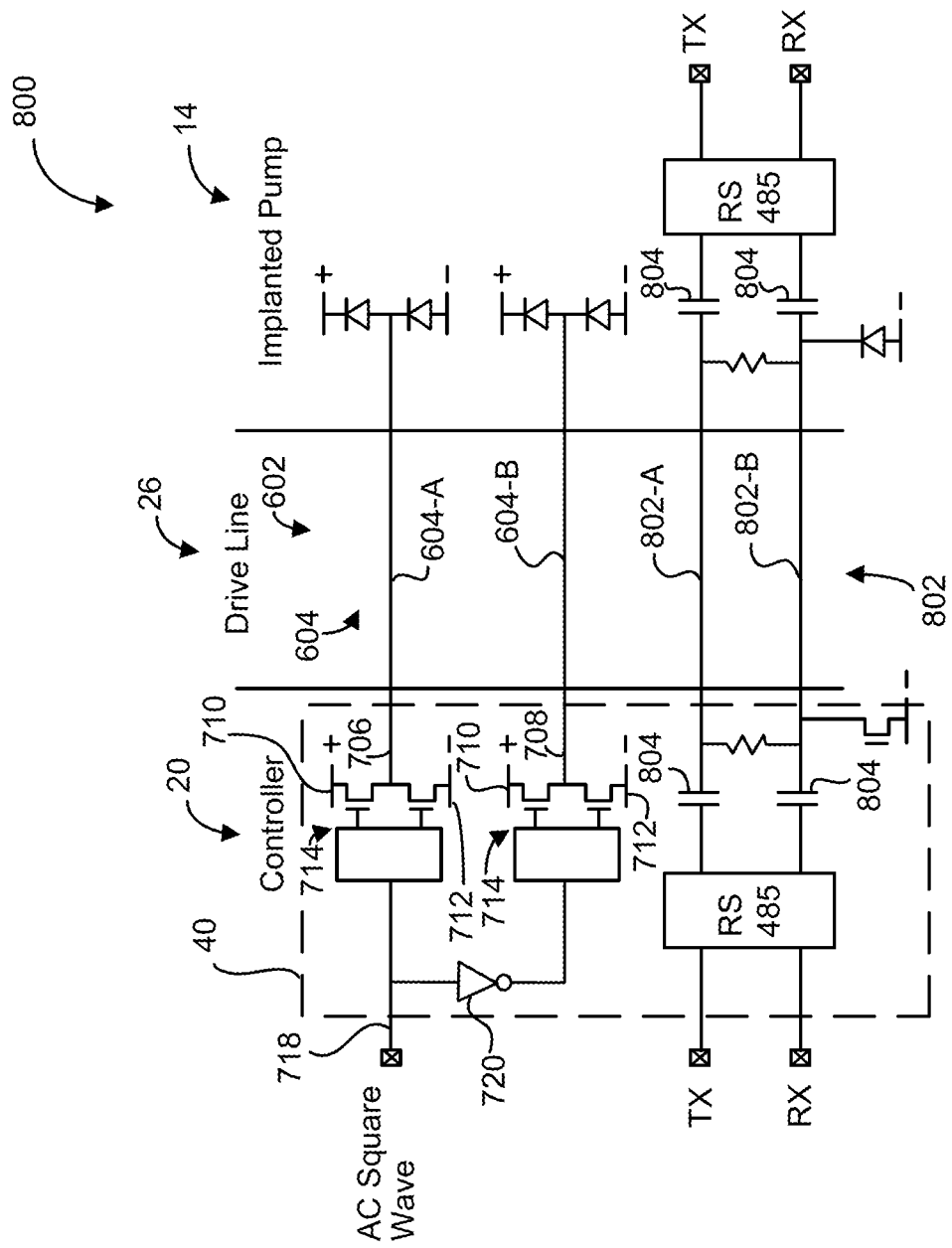
FIG. 9 is an embodiment of a system for connecting between the system controller and the implanted blood pump with a four wire driveline.

With reference now to FIG. 9, an embodiment of a system 800 for connecting between the system controller 20 and the implanted blood pump 14 with a four wire driveline 26 is shown. As seen in FIG. 9, the driveline 26 includes a plurality of wires 602. This plurality of wires 602 includes a plurality of power transmission wires 604, a plurality of communication wires 802.

As seen in FIG. 9, the system controller 20 includes the transmission module 40 that can include the first output 706 and the second output 708. The first output 706 can connect to the first power transmission wire 604-A and the second output 708 can connect to the second power transmission wire 604-B. As further seen, each of the first output 706 and the second output 708 can be selectively connected to the positive voltage source 710 and/or the negative voltage source 712, via the plurality of switches 714. The control of these plurality of switches 714 can result in one or both of the first output 706 and the second output 708 having a positive or negative voltage. In some embodiments, the plurality of switches 714 controlling the voltage of the first output 706 can be controlled according to a control signal received via connection 718. In some embodiments, and as seen in FIG. 9, the plurality of switches 714 controlling the voltage of the second output can connect to connection the 718 via the logic inverter 720 such that the switching of the plurality of switches 714 controlling the voltage of the second output 708 is opposite to the switching of the plurality of switches 714 controlling the voltage of the first output 706. Thus, when the first output 706 is connected to the positive voltage source 710, the second output 708 is connected to the negative voltage source 712. The controlling of the switching such that the voltage of the second output 708 is opposite to the voltage of the first output 706 creates AC electrical current in the first and second output 706, 708.

In some embodiments, the transmission module 40 can include one or several components configured to transmit and/or receive data via the plurality of communication wires 802. In some embodiments, the plurality of communication wires 802 can be operated as a differential pair to transmit and/or receive data. In some embodiments, the communication using the plurality of communication wires 802 can be performed according to one or several communication standards such as, for example, RS-485. In some embodiments, and to further prevent electrolysis arising from the presence of a DC current in the guide wire 26, the plurality of communication wires 802 can be operated without a DC bias. In some embodiments, this can be achieved via the inclusion of capacitors 804 in one or both of the system controller 20 and the implanted blood pump 14 and connecting to one of or more of the plurality of communication wires 802. As depicted in FIG. 9, each of the plurality of communication wires 802 is associated with a capacitor 804 in the system controller 20 and a capacitor 804 in the implanted blood pump 14.

In some embodiments, and to further prevent the existence of a DC current through the plurality of communication wires, data transmitted via the communication wires can be encoded to eliminate any DC bias. In one embodiment, for example, this can include communicating between the system controller 20 and the implanted blood pump 14 according to a phase encoding scheme, or more specifically communicating between the first transceiver and the second transceiver according to a phase encoding schemes such as, for example, Manchester coding.

In some embodiments in which one or several of the power transmission wires 604 fails and/or faults, one or several of the communication wires 802 can be reconfigured to operate as a power transmission wire 604. In some embodiments, this can include the termination of communication via a differential pair of the plurality of communication wires. Specifically, in some embodiments, in the event one of the plurality of power transmission wires 604 fails and/or faults, a first communication wire 802-A can be reconfigured for use as a power transmission wire 604. In some embodiments, this can include alternatingly connecting the first communication wire 802-A to the positive voltage source 710 and the negative voltage source 712 via plurality of switches 714. In some embodiments, this plurality of switches 714 can be controlled to, in combination with the control of the plurality of switches 714 of the remaining non-failed and/or non-faulted power transmission line 604 to provide AC electrical power to the implanted blood pump 14. In some embodiments, this can further include communication via a second communication wire 802-B and/or communication via modulation of the AC electrical power to encode data in the provided AC electrical power and/or the overlaying of a data signal on top of the AC electrical power.

Alternatively, in some embodiments, failure and/or fault of one of the power transmission wire 604 can result in a change from providing AC electrical power to providing DC electrical power. In such an embodiment, one of the communication wires 802 can be held at a constant voltage such as, for example, a constant voltage of 0 V and the non-failed and/or non-faulted one of the power transmission wires 604 can be held at a constant high-voltage such as, for example, 1 V, 2 V, 3 V, 4 V, 5 V, 6 V, 7 V, 8 V, 9 V. 10 V, 15 V, 20 V, 50 V, 100 V, and/or any other or intermediate voltage. In such an embodiment, the plurality of communication wires 802 can continue operation as differential pair and the one of the communication wires 802 held to a constant voltage can also serve as a power transmission wire 604. Thus, in this embodiment, in the event of the detection of a failure and/or fault of one or more of the plurality of wires 602 and specifically of one or more of the power transmission wires 604, one of the communication wires 802 can be reconfigured as a power transmission wire 602 and can be specifically reconfigured as a dual power transmission wire and communication wire.

In some embodiments, the system 800 can be a mechanical circulatory support system for providing modulated AC power and control signals to the implantable blood pump 14. This implantable blood pump can include: a DC powered pump control unit 130 that can control the implantable blood pump 14 according to one or several stored instructions; a rectifier 614 that can be electrically connected to the pump control unit 130, which implantable rectifier 614 is can convert all or portions of the received AC to DC for powering the pump control unit 130. The system can include an external controller 20 that can be electrically connected to the rectifier 130 via, for example, the driveline 602. The external controller 20 can provide AC electrical power to the implantable blood pump 14.

The driveline 602 can include a pair of power transmission wires 604, and a pair of communication wires 802. Each of the pair of power transmission wires 604 can connect to an output 706, 708 of the external controller 20. Specifically, the first output 706 can connect to the first power transmission wire 604-A and the second output 708 can connect to the second power transmission wire 604-B. Each of these outputs 706, 708 can be switchably connected to the positive voltage source 710 and/or the negative voltage source 712, via the plurality of switches 714, which plurality of switches 714 can be controlled to generate AC electrical power in the power transmission wires 604 of a desired frequency.

The pair of communication wires 802 can be operated as a differential pair to transmit and/or receive data. Specifically, the communication using the pair of communication wires 802 can be performed according to one or several communication standards such as, for example, RS-485. The communications wires 802 can connect to a transceiver in the transmission module 40 and/or to a transceiver and/or receiver in the implantable blood pump 14. In some embodiments, each of the communication wires 802 can connect to a capacitor 804 that prevents creation of a DC bias in the communication wires 802. As seen in FIG. 9, the first communication wire 802-A can connect to the external controller 20 via a first capacitor and can connect to the implantable blood pump 14 via a second capacitor. Similarly, the second communication wire 802-B can connect to the external controller 20 via a first capacitor and can connect to the implantable blood pump 14 via a second capacitor. One or both of the communication wires 802 can be reconfigurable to operate as a power transmission line, and thus can be switchably connectable to the positive voltage source 710 and/or the negative voltage source 712, via the plurality of switches 714

Figure 10:
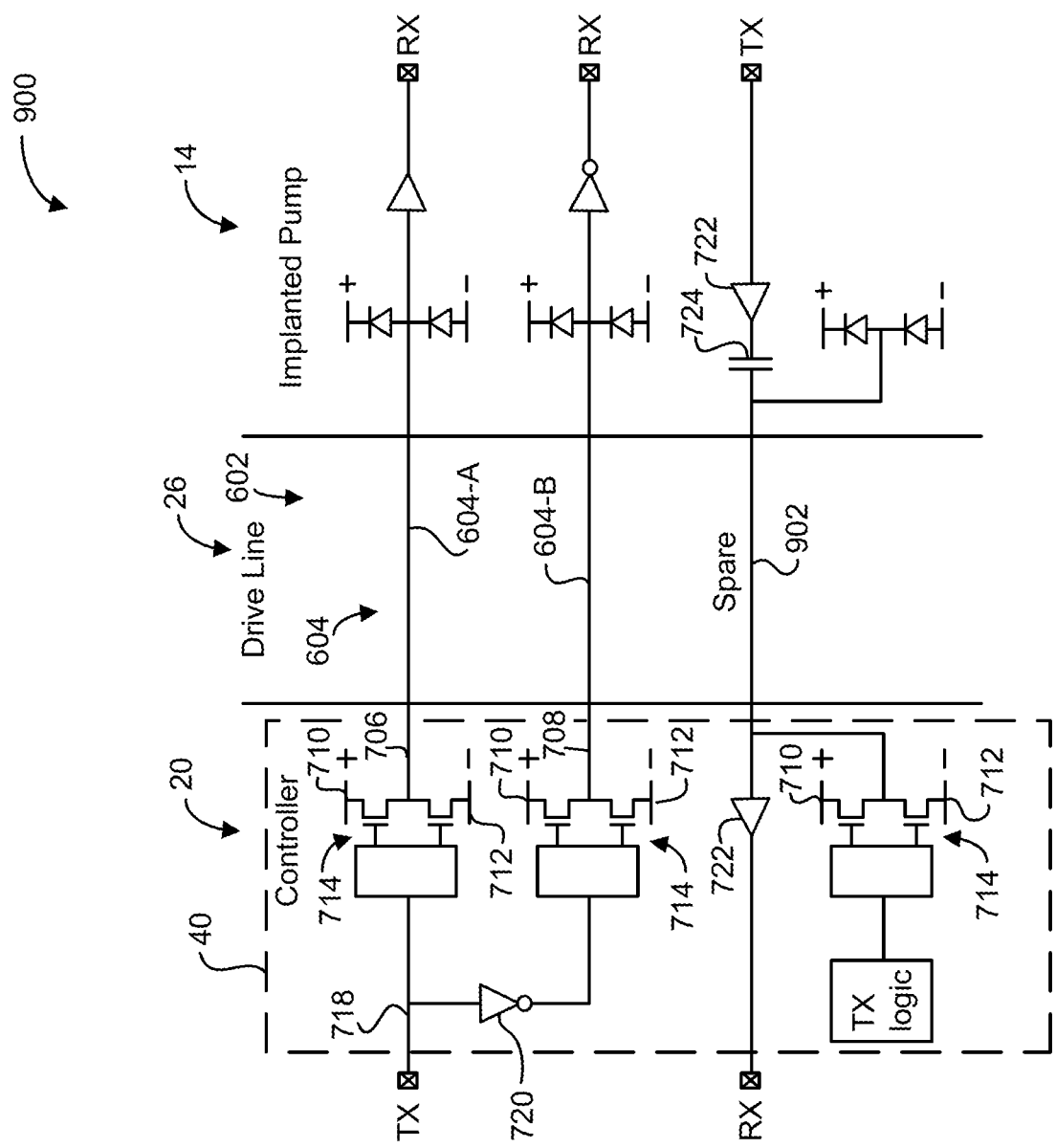
FIG. 10 is a schematic illustration of one embodiment of a system for connecting the system controller and the implanted blood pump via the driveline.

With reference now to FIG. 10, a schematic illustration of one embodiment of a system 900 for connecting the system controller 20 to the implanted blood pump 14 via the driveline 26 is shown. As seen in FIG. 10, the driveline 26 includes a plurality of wires 602 including a plurality of power transmission wires 604 and a single communication wire 902.

As seen in FIG. 10, the system controller 20 includes the transmission module 40 that can include the first output 706 connecting to the first power transmission wire 604-A and the second output 708 connecting to the second power transmission wire 604-B. As further seen, each of the first output 706 and the second output 708 can be selectively connected to the positive voltage source 710, and/or the negative voltage source 712 via the plurality of switches 714. The control of these plurality of switches 714 can result in one or both of the first output 706 and the second output 708 having a positive or negative voltage.

In some embodiments, the plurality of switches 714 controlling the voltage of the first output 706 can be controlled according to a control signal received via the connection 718. In some embodiments, and as seen in FIG. 10, the plurality of switches 714 controlling the voltage of the second output can connect to the connection 718 via the logic inverter 720 such that the switching of the plurality of switches 714 controlling the voltage of the second output 708 is opposite to the switching of the plurality of switches 714 controlling the voltage of the first output 706. Thus, when the first output 706 is connected to the positive voltage source 710, the second output 708 is connected to the negative voltage source 712. The controlling of the switching such that the voltage of the second output 708 is opposite to the voltage of the first output 706 creates AC electrical current in the first and second output 706, 708.

The single communication wire 902 shown in FIG. 10 can be configurable for use as a communication wire and/or as a power transmission wire. In some embodiments, the single communication wire 902 can include one or several direction flow elements such as diodes 722, and a capacitor 724. In some embodiments, the single communication wire 902 can be switchably connected to one or both of the positive voltage source 710 and the negative voltage source 712 via a plurality of switches 714. In some embodiments, and when the single communication wire is being operated as a communication wire, the plurality of switches 714 are not controlled to selectively connect the communication wire 902 to either the positive voltage source 710 or the negative voltage source 712, but rather the plurality of switches 714 can be held open. In the event that a failure and/or fault of one of the plurality of power transmission wires 604 is detected, the single communication wire 902 can be reconfigured as a power transmission wire 604 by controlling the plurality of switches to selectively connect the single communication wire 902 to either the positive voltage source 710 or the negative voltage source 712. In some embodiments, this selective connection of the single communication wire 902 to either the positive voltage source 710 or the negative voltage source 712 can be coordinated with the selective connection of the remaining power transmission wire 694 such that AC electrical power is generated through the drive line 26.

In some embodiments, the system 900 depicted in FIG. 10 can communicate from the system controller 20 to the implanted blood pump 14 via the power transmission wires 604 by the modulating of the AC electrical power to contain data in the AC electrical power and/or by the overlaying of a data signal on the AC electrical power as discussed above. In some embodiments, communication from the implanted blood pump 14 to the system controller 20 can occur via the single communication wire 902. In the event that the single communication wire 902 is reconfigured to operate as a power transmission wire 604, the ability to communicate data from the implanted blood pump 14 to the system controller 20 may be limited or nonexistent. Thus, in some embodiments, the driveline 26 does not include a wire whereby data is communicable from the implantable blood pump 14 to the system controller 20 when the single communication wire is reconfigured as a power transmission wire.

In such an embodiment, as well as in other embodiments disclosed herein, the identification of a fault and/or failure can result in a reconfiguration of the phase of provided AC electrical power and/or a reconfiguration of the functioning of one or several of the plurality of wires 602 of the driveline 26. In some embodiments, this reconfiguration can be accompanied by an alert to a user such as the individual in which implanted blood pump 14 is implanted and/or a doctor or caregiver associated with or responsible for that individual. This alert can identify, for example, the date and time of the identified fault and/or failure and a reconfiguration in response to that identified fault and/or failure. In embodiments in which the plurality of communication wires comprise a single communication wire 902 as depicted in FIG. 10, this alert can further indicate a loss of ability to receive data from the implanted blood pump 14 and/or can indicate a degradation to the ability to communication between the system controller 20 and the implanted blood pump 14.

In some embodiments, the system 900 can be a mechanical circulatory support system for providing modulated AC power and control signals to the implantable blood pump 14. This implantable blood pump can include: a DC powered pump control unit 130 that can control the implantable blood pump 14 according to one or several stored instructions; a rectifier 614 that can be electrically connected to the pump control unit 130, which implantable rectifier 614 is can convert all or portions of the received AC to DC for powering the pump control unit 130. The system can include an external controller 20 that can be electrically connected to the rectifier 130 via, for example, the driveline 602. The external controller 20 can provide AC electrical power to the implantable blood pump 14.

The driveline 602 can include a pair of power transmission wires 604, and a communication wire 902. Each of the pair of power transmission wires 604 can connect to an output 706, 708 of the external controller 20. Specifically, the first output 706 can connect to the first power transmission wire 604-A and the second output 708 can connect to the second power transmission wire 604-B. Each of these outputs 706, 708 can be switchably connected to the positive voltage source 710 and/or the negative voltage source 712, via the plurality of switches 714, which plurality of switches 714 can be controlled to generate AC electrical power in the power transmission wires 604 of a desired frequency.

The communication wire 902 can be configurable for use as a communication wire and/or as a power transmission wire. The communication wire can be connected to one or several direction flow elements, which one or several direction flow elements can be two diodes 722, and a capacitor 724. The communication wire 092 can be reconfigurable to operate as a power transmission line, and thus can be switchably connectable to the positive voltage source 710 and/or the negative voltage source 712, via the plurality of switches 714.

Figure 11:
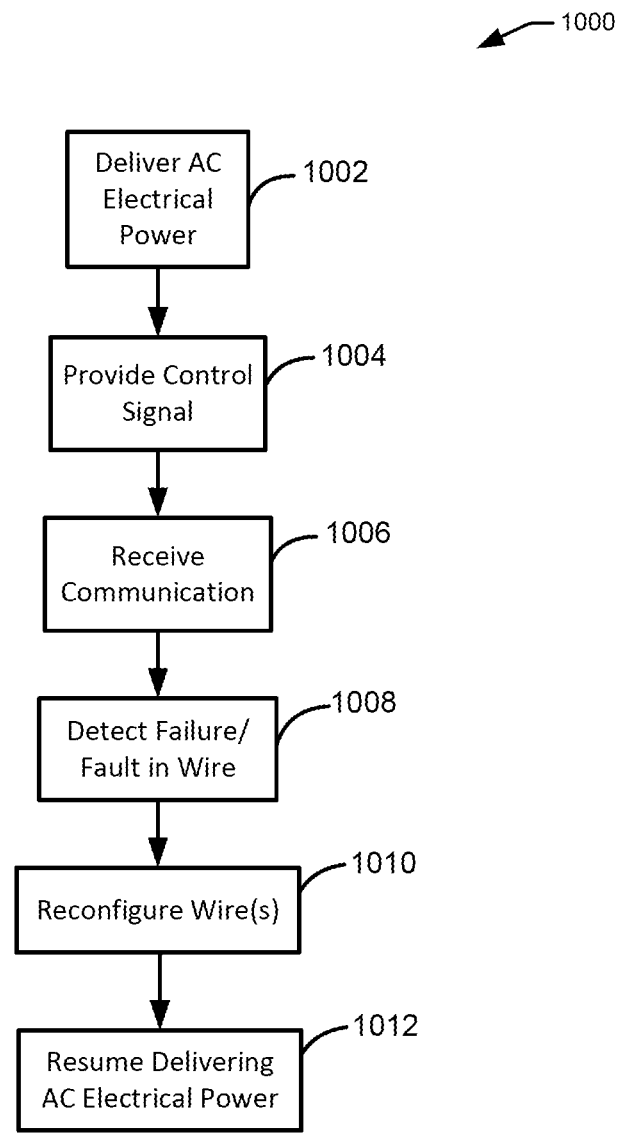
FIG. 11 is a flowchart illustrating one embodiment of a process for reconfiguring wires in a driveline.

With reference now to FIG. 11, a flowchart illustrating one embodiment of a process 1000 for reconfiguring wires is shown. The process 1000 can be performed by the system controller 20 in connection with the drive line 26 and/or the implanted blood pump 14. The process 1000 begins at block 1002, wherein AC electrical power is delivered. In some embodiments, the delivery of AC electrical power can include the controlling of the plurality of switches 714 to generate AC electrical power through the driveline 26. In some embodiments, this controlling of the plurality of switches can include generating one or several control signals that control the opening and closing of some or all of the plurality of switches 714. In some embodiments, this AC electrical power can be single phase, dual phase, three-phase, multiphase, or the like.

While the AC electrical power is delivered, the process 1000 proceeds to block 1004 wherein one or several control signals are provided from the system controller 20 to the implanted blood pump 14 via the driveline 26. These one or several control signals can, when received by the implanted blood pump 14, alter the operation of the implanted blood pump 14. In some embodiments, these one or several control signals can be provided via the power transmission wires 604 and/or via one or several communication wires. In some embodiments in which the communication wires comprise two or more communication wires, these one or several control signals can be sent via the operation of the two or more communication wires as a differential pair.

After and/or simultaneous with the providing of control signals, the process 1000 can proceed to block 1006 and the system controller 20 can receive one or several communications from the implanted blood pump 14 via the driveline 26. In some embodiments, these one or several communications can comprise data relating to the operation and/or performance of the implanted blood pump. In some embodiments, these communications can be received via the plurality of power transmission wires 604 and/or via one or several communication wires. In some embodiments, such as when the communication wires comprise a single communication wire, the control signals provided in block 1004 can be provided via the power transmission wires and the communications can be received via the communication wires. In some embodiments in which the communication wires comprise two or more communication wires, these one or several communications can be received via the operation of the two or more communication wires as a differential pair.

After and/or simultaneous with the receipt of communications, the process 1000 proceeds to block 1008 wherein a failure and/or fault in a wire is detected. In some embodiments, the failure and/or fault can comprise a short, a breakage, or the like. In some embodiments, the failure and/or fault can be detected with a processor in the system controller 20 which can, for example, monitor voltage and/or current at different locations in the system controller 20, the driveline 26, and/or the implanted blood pump 14.

When the fault and/or failure is detected, the process 1000 proceeds to block 1010 wherein one or several of the plurality of wires 602 are reconfigured. In some embodiments, this can include the reconfiguring and specifically the reduction of the phase of the provided AC electrical power such as, for example, switching from three-phase AC electrical power to single phase AC electrical power. In some embodiments, this can further include switching from providing AC electrical power to providing DC electrical power. In some embodiments, the reconfiguring of the plurality of wires 602 can include reconfiguring one or several power transmission wires 604 to function as one or several communication wires and/or reconfiguring one or several communication wires to function as one or several power transmission wires 604. In some embodiments, the reconfiguring of the plurality of wires 602 can further include reconfiguring a wire to function as a dual power transmission and communication wire and/or the reconfiguring of the designated spare wire to function as either a power transmission wire or a communication wire. In some embodiments, this reconfiguration can include controlling of switches associated with the reconfigured wire to begin delivering AC electrical power through the reconfigured wire and/or controlling the reconfigured wire to transmit control signals and/or communications. In some embodiments, the reconfiguring of the wires can include the generating and sending of an alert to the user of the implanted blood pump 14 and/or to an individual associated with and/or responsible for the user of the implanted blood pump 14. In some embodiments, this alert can identify the detected fault and/or failure, the time of the detected fault and/or failure, and/or any reconfigurations taken in response to the detected fault and/or failure.

After the wires have been reconfigured, the process 1000 proceeds block 1012 wherein the delivery of AC electrical power is resumed. In some embodiments, this can include the return to block 1002 in proceeding with the process as outlined above.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A mechanical circulatory support system comprising:
   an implantable blood pump comprising a rectifier and a direct current (DC) powered pump control unit configured to control the implantable blood pump according to one or several stored instructions, wherein the rectifier is configured to generate a DC electrical power supplied to the DC powered pump control unit from an alternating current (AC) electrical power;
   a driveline electrically connected to the implantable blood pump, wherein the driveline comprises a plurality of power transmission wires and a communication wire, and wherein the communication wire is reconfigurable as a power transmission wire; and
   an external controller electrically connected to the plurality of power transmission wires and the communication wire, wherein the external controller is configured to output the AC electrical power for transmission to the rectifier through the plurality of power transmission wires in a first operational mode and output the AC electrical power for transmission to the rectifier through the communication wire and at least one of the plurality of power transmission wires in a second operational mode.

2. The mechanical circulatory support system of claim 1, wherein the communication wire is reconfigurable as a power transmission wire by the external controller.

3. The mechanical circulatory support system of claim 1, wherein the AC electrical power is multiphase.

4. The mechanical circulatory support system of claim 3, wherein the plurality of power transmission wires comprise three power transmission wires.

5. The mechanical circulatory support system of claim 1, wherein the driveline comprises a second communication wire.

6. The mechanical circulatory support system of claim 5, wherein the external controller is configured to communicate according to RS-485.

7. The mechanical circulatory support system of claim 5, wherein the external controller comprises a first transceiver, wherein the DC powered pump control unit comprises a second transceiver, and wherein the first transceiver and the second transceiver are configured to operate the communication wire and the second communication wire as a differential pair.

8. The mechanical circulatory support system of claim 7, wherein the first and second transceivers are configured to communicate via phase encoding.

9. The mechanical circulatory support system of claim 1, wherein the external controller is configured to provide single phase AC electrical power to the implantable blood pump, and wherein the external controller is configured to modulate the single phase AC electrical power to communicate data to the implantable blood pump via the plurality of power transmission wires of the driveline.

10. The mechanical circulatory support system of claim 9, wherein the implantable blood pump is configured to receive data from the external controller via the plurality of power transmission wires, and wherein the implantable blood pump is configured to communicate data to the external controller via the communication wire.

11. The mechanical circulatory support system of claim 10, wherein the external controller is configured to reconfigure the communication wire as a power transmission wire.

12. The mechanical circulatory support system of claim 11, wherein the driveline does not include a wire whereby data is communicable from the implantable blood pump to the external controller when the communication wire is reconfigured as a power transmission wire.

13. The mechanical circulatory support system of claim 1, wherein the implantable blood pump comprises a magnetically levitated portion.

14. The mechanical circulatory support system of claim 1, wherein the driveline electrically connects to the implantable blood pump in a hermetically sealed housing.

15. The mechanical circulatory support system of claim 1, wherein the implantable blood pump comprises a communication transmission node and a diode, wherein the diode is connected between the communication transmission node and the communication wire to block flow of current from the communication wire to the communication transmission node.

16. The mechanical circulatory support system of claim 15, wherein the implantable blood pump comprises a capacitor connected between the diode and the communication wire to inhibit formation of a DC bias in the communication wire.

17. The mechanical circulatory support system of claim 1, wherein the implantable blood pump comprises a capacitor connected to the communication wire to inhibit formation of a DC bias in the communication wire.

18. The mechanical circulatory support system of claim 1, wherein the external controller is configured to generate the AC electrical power from an input DC electrical power.

* * * * *